(12) United States Patent
Pandey et al.

(10) Patent No.: US 8,906,343 B2
(45) Date of Patent: *Dec. 9, 2014

(54) PAA NANOPLATFORMS CONTAINING FLUOROPHORES AND TARGETED MOIETIES COVALENTLY LINKED AND PHOTOSENSITIZER POST-LOADED

(75) Inventors: Ravindra K. Pandey, East Amherst, NY (US); Raoul Kopelman, Ann Arbor, MI (US); Anurag Gupta, Hamburg, NY (US); Munawwar Sajjad, Clarence Center, NY (US)

(73) Assignees: Health Research, Inc., Buffalo, NY (US); The Research Foundation of State University of New York, Amherst, NY (US); Regents of the University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/566,444

(22) Filed: Aug. 3, 2012

(65) Prior Publication Data

US 2013/0195758 A1 Aug. 1, 2013

Related U.S. Application Data

(63) Continuation-in-part of application No. 12/909,573, filed on Oct. 21, 2010, now Pat. No. 8,562,944.

(60) Provisional application No. 61/279,522, filed on Oct. 21, 2009.

(51) Int. Cl.
| | |
|---|---|
| *A61K 51/06* | (2006.01) |
| *A61K 49/12* | (2006.01) |
| *A61K 49/00* | (2006.01) |
| *A61K 41/00* | (2006.01) |
| *A61K 47/48* | (2006.01) |
| *A61K 51/12* | (2006.01) |
| *A61K 51/04* | (2006.01) |
| *B82Y 5/00* | (2011.01) |
| *B82Y 15/00* | (2011.01) |

(52) U.S. Cl.
CPC ........... *A61K 51/065* (2013.01); *A61K 41/0071* (2013.01); *A61K 47/489* (2013.01); *B82Y 5/00* (2013.01); *A61K 49/00* (2013.01); *A61K 49/0002* (2013.01); *A61K 51/1244* (2013.01); *B82Y 15/00* (2013.01); *A61K 49/0093* (2013.01); *A61K 51/0451* (2013.01); *A61K 49/0032* (2013.01); *A61K 49/126* (2013.01); *A61K 49/0052* (2013.01)
USPC ............ 424/1.85; 424/9.3; 424/9.6; 525/279; 525/54.1; 525/54.2

(58) Field of Classification Search
CPC . A61K 41/0057; A61K 51/065; A61K 49/00; A61K 49/126
See application file for complete search history.

(56) References Cited

U.S. PATENT DOCUMENTS

2005/0196343 A1* 9/2005 Reddy et al. ............... 424/9.322

FOREIGN PATENT DOCUMENTS

WO WO2009105209 * 8/2009 ........... A61K 31/695

OTHER PUBLICATIONS

Kopelman, Raoul, et al., "Multifunctional Nanoparticle Platforms for In Vivo MRI Enhancement and Photodynamic Therapy of a Rat Brain Cancer", Journal of Magnetism and Magnetic Materials 293, pp. 404-410, Copyright 2005.
Daubresse, Catherine, et al., "Enzyme Immobilization in Nanoparticles Produced by Inverse Microemulsion Polymerization", Journal of Colloid and Interface Science 168, pp. 222-229, Copyright 1994.
Gupta et al., "Multifunctional ORMOSIL and PAA Nanoparticles", Photodynamic Therapy: Back to the Future, Edited by Kessel, David H., Proceedings of the SPIE, vol. 7380 (2009), pp. 73805H-73805H-12 (2009).

* cited by examiner

*Primary Examiner* — Suzanne Ziska
*Assistant Examiner* — Thurman Wheeler
(74) *Attorney, Agent, or Firm* — Michael L. Dunn

(57) ABSTRACT

A PAA nanoparticle containing a covalently linked fluorescent dye and a post-loaded tetrapyrrolic photosensitizer.

18 Claims, 35 Drawing Sheets
(9 of 35 Drawing Sheet(s) Filed in Color)

PAA NANOPLATFORMS CONTAINING FLUOROPHORES AND TARGETED MOIETIES COVALENTLY LINKED AND PHOTOSENSITIZER POST-LOADED

CROSS-REFERENCE TO RELATED APPLICATIONS

This application is a continuation-in-part of U.S. patent application Ser. No. 12/909,573 filed Oct. 21, 2010 which in turn claims the benefit under 35 U.S.C. §119(e) of U.S. Provisional Application No. 61/279,522, filed Oct. 21, 2009 which applications are incorporated by reference herein in their entirety.

STATEMENT REGARDING FEDERALLY SPONSORED RESEARCH OR DEVELOPMENT

This invention was made with government support under Grant Numbers CA119358 and CA114053 awarded by the National Institutes of Health. The government has certain rights in the invention.

BACKGROUND OF THE INVENTION

Nanoscience is being developed in conjunction with advanced medical science for further precision in diagnosis and treatment. Nanoplatforms and nanovectors that deliver a therapeutic or imaging agent for biomedical applications show promise for cancer diagnosis and therapy. Therapeutic examples include nanoparticle containing PDT agents, folate receptor-targeted, boron containing dendrimers for neutron capture and nanoparticle-directed thermal therapy.

Nanoparticles have had disadvantages when considered for use in photodynamic therapy (PDT). In particular, certain nanoparticles have no relatively large knowledge base on cancer imaging, PDT, chemical sensing, stability and biodegradation. (2) have in in-vivo toxicity. (3) Have short plasma circulation time without surface modification and unstable or uncontrollable biodegradation and bioelimination rates (4) Have problems associated with scale-up and are not storage stabile over extended periods. And (5) have additional limitations including relative difficulty in incorporating hydrophobic compounds, leaching of small hydrophilic components unless they are "anchored", and unknown limitation on bulk tumor permeability because of hydrogel swelling.

A major challenge of cancer therapy is preferential destruction of malignant cells with sparing of normal tissue. Critical for successful eradication of malignant disease are early detection and selective ablation of the malignancy. Photodynamic therapy (PDT) is a clinically effective and still evolving locally selective therapy for cancers. The utility of PDT has been demonstrated with various photosensitizers for multiple types of disease. It is FDA approved for early and late stage lung cancer, obstructive esophageal cancer, high-grade dysplasia associated with Barrett's esophagus, age-related macular degeneration and actinic keratoses. PDT employs tumor localizing photosensitizers that produce reactive singlet oxygen upon absorption of light which is believed to be responsible for the destruction of the tumor. Subsequent oxidation-reduction reactions also can produce superoxide anions, hydrogen peroxide and hydroxyl radicals which contribute to tumor ablation4. Photosensitizers have been designed which localize relatively specifically to certain subcellular structures such as mitochondria, which are highly sensitive targets. On the tumor tissue level, direct photodynamic tumor cell kill, destruction of the tumor supporting vasculature and possibly activation of the innate and adaptive anti-tumor immune system interact to destroy the malignant tissue6. The preferential killing of the targeted cells (e.g. tumor), rather than adjacent normal tissues, is essential for PDT, and the preferential target damage achieved in clinical applications is a major driving force behind the use of the modality. The success of PDT relies on development of tumor-avid molecules that are preferentially retained in malignant cells but cleared from normal tissues.

Malignant brain tumors (gliomas) are generally resistant to conventional aggressive treatments by surgery, radiation, and chemotherapy. Over 80% of recurrences are within 2 cm of the original tumor margin. The prognosis after glioma surgery is partly determined by the precision of surgical resection, which may be sub-optimal since the intra-operative identification of tumor margins or small foci of cancer cells depends on visual inspection. Given the potent nature of brain tumors, better treatments are essential to improve response. Photodynamic therapy (PDT) for the treatment of a variety of brain tumors, in particular gliomas have been investigated in laboratory studies and clinical trials. The main advantage of PDT lies in its ability to select out tumor cells that are infiltrating brain parenchyma and that are responsible for local tumor recurrence, which is the main therapeutic dilemma in the treatment of gliomas.

In efforts to develop effective photosensitizers with the required photophysical characteristics, compounds having a tetrapyrrolic core ring were used. Usually, chlorophyll-a and bacteriochlorophyll-a were used as intermediates in synthesis. Extensive QSAR studies on a series of the alkyl ether derivatives of pyropheophorbide-a (660 nm) led to selection of HPPH (hexyl ether derivative), now in promising Phase II clinical trials. Photosensitizer development now extends to purpurinimide (700 nm) and bacteriopurpurinimde (780-800 nm) series with high singlet oxygen producing capability. Long wavelength absorption is important for treating large deep seated tumors, because longer wavelength light increases penetration and minimizes the number of optical fibers needed for light delivery within the tumor.

Various efforts have been made to target tumor cells so that an agent may destroy the tumor cells while sparing normal cells. Such systems are reliant upon specific receptors and as such must reach receptor location. This is a disadvantage since even though the agent may reach the targeted cell, it may not be effective unless the particular receptor is reached and bound.

Multiple, complementary techniques for tumor detection, including magnetic resonance, scintigraphic and optical imaging are under active development. Each approach has particular strengths and advantages. Optical imaging includes measurement of absorption of endogenous molecules (e.g. hemoglobin) or administered dyes, detection of bioluminescence in preclinical models, and detection of fluorescence from endogenous fluorophores or from targeted exogenous molecules. Fluorescence, the mission of absorbed light at a longer wavelength, can be highly sensitive: a typical cyanine dye with a lifetime of 0.6 nsec can emit up to 1032 photons/second/mole. A sensitive optical detector can image <103 photons/second. Thus even with low excitation power, low levels of fluorescent molecular beacons can be detected. A challenge is to deliver the dyes selectively and in high enough concentration to detect small tumors. Use of ICG alone to image hypervascular or "leaky" angiogenic vessels around tumors has been disappointing, due to its limited intrinsic tumor selectivity. Multiple approaches have been employed to improve optical probe-localization, including administering it in a quenched form that is activated within tumors, or coupling it to antibodies or small molecules such as receptor ligands. Recent studies have focused on developing dye conjugates of small bioactive molecules, to improve rapid diffusion to target tissue and use combinatorial and high throughput strategies to identify, optimize, and enhance in vivo stability of the new probes. Some peptide analogs of ICG derivatives have moderate tumor specificity and are entering pre-clinical studies. However, none of these compounds are designed for both tumor detection and therapy. It is important to develop targeting strategies that cope with the heterogeneity of tumors in vivo, where there are inconsistent and varying expressions of targetable sites.

Photosensitizers (photosensitizer) generally fluoresce and their fluorescence properties in vivo has been exploited for the detection of early-stage cancers in the lung, bladder and other sites. For treatment of early disease or for deep seated tumors the fluorescence can be used to guide the activating light. However, photosensitizers are not optimal fluorophores for tumor detection for several reasons: (i) They have low fluorescence quantum yields (especially the long wavelength photosensitizers related to bacteriochlorins). Efficient photosensitizer tend to have lower fluorescence efficiency (quantum yield) than compounds designed to be fluorophores, such as cyanine dyes because the excited singlet state energy emitted as fluorescence is instead transferred to the triplet state and then to molecular oxygen. (ii) They have small Stokes shifts. Porphyrin-based photosensitizer have a relatively small difference between the long wavelength absorption band and the fluorescence wavelength (Stokes shift), which makes it technically difficult to separate the fluorescence from the excitation wavelength. (iii) Most photosensitizers have relatively short fluorescent wavelengths, <800 nm, which are not optimal for detection deep in tissues.

Attempts have been made to develop bifunctional conjugates that use tumor-avid photosensitizer to target the NIR fluorophores to the tumor. The function of the fluorophore is to visualize the tumor location and treatment site. The presence of the photosensitizer allows subsequent tumor ablation. The optical imaging allows the clinician performing PDT to continuously acquire and display patient data in real-time. This "see and treat" approach may determine where to treat superficial carcinomas and how to reach deep-seated tumors in sites such as the breast, lung and brain with optical fibers delivering the photo-activating light. A similar approach was also used for developing potential PDT/MRI conjugates in which HPPH was conjugated with Gd(III)DTPA Due to a significant difference between imaging and therapeutic doses, the use of a single molecule that includes both modalities is problematic.

Positron emission tomography (PET) is a technique that permits non-invasive use of radioisotope labeled molecular imaging probes to image and assay biochemical processes at the level of cellular function in living subjects20. PET predominately has been used as a metabolic marker, without specific targeting to malignancies. Recently, there has been growing use of radiolabeled peptide ligands to target malignancies. Currently, PET is important in clinical care and is a critical component in biomedical research, supporting a wide range of applications, including studies of tumor hypoxia, apoptosis and angiogenesis21. For targeting, a long circulation time may be desirable, as it can increase delivery of the agent into tumors. HPPH and the iodobenzyl pheophorbide-a have plasma half lives ~25 h. The long radiological half life of $^{124}$I is well matched to the pheophorbides; it permits sequential imaging with time for clearance from normal tissue. Labeling techniques with radioiodine are well defined with good yield and radiochemical purity22. Despite the complex decay scheme of $^{124}$I which results in only 25% abundance of positron (compared with 100% positron emission of 18F), in vivo quantitative imaging with $^{124}$I labeled antibodies has been successfully carried out under realistic conditions using a PET/CT scanner A variety of biomolecules have been labeled with $^{124}$I. We have devised a coupling reaction which rapidly and efficiently links $^{124}$I to a tumor-avid photosensitizer23-25, and used the conjugate to target and image murine breast tumor and its metastasis to lung Acquisition of clinical PET images can be slow, but combination PET-CT scanners allow real time guidance of therapeutic interventions. Also, new developments in tracking may permit real time interventions guided by PET data sets.

BRIEF SUMMARY OF THE INVENTION

The present invention relates to polyacrylic acid (PAA) nanoparticles containing a photosensitizer and an imaging enhancing agent.

In accordance with the invention, therapeutic and imaging potential of encaphotosensitizerulated, post-loaded and covalently linked photosensitizer-nanoparticles have been evaluated. In PAA nanoparticle the post-loading efficiency showed enhanced in vitro/in vivo therapeutic and imaging potential. PAA nanoparticle have core matrixes that can readily incorporate molecular or small nanoparticle payloads, and can be prepared in 10-150 nm sizes, with good control of size distributions. The surfaces of nanoparticles can be readily functionalized, to permit attachment of targeting ligands, and both are stable to singlet oxygen (1O2) produced during photodynamic therapy (PDT). PAA-nanoparticles, i.e. poly(acrylic acid) nanoparticles, have the advantages of (1) A relatively large knowledge base on cancer imaging, PDT, chemical sensing, stability and biodegradation. (2) No known in-vivo toxicity. (3) Long plasma circulation time without surface modification, but with biodegradation and bioelimination rates controllable via the type and amount of selective cross-linking (introduced during polymerization inside reverse micelles). (4) Scale-up to 400 g material has been demonstrated, as well as storage stability over extended periods. Limitations have included relative difficulty in incorporating hydrophobic compounds, leaching of small hydrophilic components unless they are "anchored", and unknown limitation on bulk tumor permeability because of hydrogel swelling.

In accordance with the invention, photosensitizers have several very desirable properties as therapeutic agents deliverable by PAA nanoparticles. In particular, (1) Only a very small fraction of administered targeted non-photodynamic drug makes it to tumor sites and the remainder can cause systemic toxicity. However, PDT provides dual selectivity in that the photosensitizer is inactive in the absence of light and is innocuous without photoactivation. Thus the photosensitizer contained by the nanoparticle can be locally activated at the site of disease. (2) PDT effects are due to production of singlet oxygen, which, in accordance with the compounds and methods of the invention, can readily diffuse from the pores of the nanoparticle. Thus, in contrast to chemotherapeutic agents, release of encaphotosensitizerulated drug from the nanoparticle, is not necessary. Instead, stable nanoparticles with long plasma residence times can be used, which increases the amount of drug delivered to the tumors. (3) PDT is effective regardless of the intracellular location of the photosensitizer. While mitochondria are a principal target of singlet oxygen, photosensitizer incorporated in lysosomes are also active the photodynamic process causes rupture of the lysosomes with release of proteolytic enzymes and redistribution of the photosensitizer within the cytoplasm. nanoparticle platforms also provide significant advantages for PDT: (1) High levels of imaging agents can be combined with the photosensitizer in the nanoparticle permitting a "see and treat" approach, with fluorescence image guided placement of optical fibers to direct the photoactivating light to large or subsurface tumors, or to early non clinically evident disease. (2) It is possible to add targeting moieties, such as cRGD or F3 peptide to the nanoparticle so as to increase the selective delivery of the photosensitizer. (3) The nanoparticle can carry large numbers of photosensitizers, and their surface can be modified to provide the desired hydrophilicity for optimal plasma pharmacokinetics. Thus, they can deliver high levels of photosensitizer to tumors, reducing the amount of light necessary for tumor cure.

The photosensitizer is preferably a tetrapyrrolic photosensitizer having the structural formula:

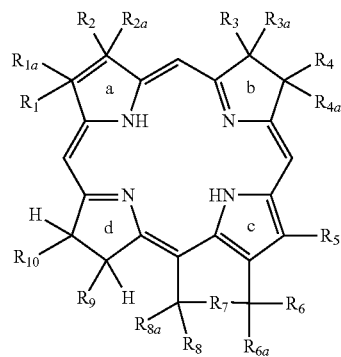

or a pharmaceutically acceptable derivative thereof, wherein:

$R_1$ and $R_2$ are each independently substituted or unsubstituted alkyl, substituted or unsubstituted alkenyl, —C(O)$R_a$ or —COOR$_a$ or —CH(CH$_3$)(OR$_a$) or —CH(CH$_3$)(O(CH$_2$)$_n$XR$_a$) where $R_a$ is hydrogen, substituted or unsubstituted alkyl, substituted or unsubstituted alkenyl, substituted or unsubstituted alkynyl, or substituted or unsubstituted cycloalkyl; where $R_2$ may be —CH=CH$_2$, —CH(OR$_{20}$)CH$_3$, —C(O)Me, —C(=NR$_{21}$)CH$_3$ or —CH(NHR$_{21}$)CH$_3$ where X is an aryl or heteroaryl group;

n is an integer of 0 to 6;

where $R_{20}$ is methyl, butyl, heptyl, docecyl or 3,5-bis(trifluoromethyl)-benzyl; and $R_{21}$ is 3,5,-bis(trifluoromethyl)benzyl;

$R_{1a}$ and $R_{2a}$ are each independently hydrogen or substituted or unsubstituted alkyl, or together form a covalent bond;

$R_3$ and $R_4$ are each independently hydrogen or substituted or unsubstituted alkyl;

$R_{3a}$ and $R_{4a}$ are each independently hydrogen or substituted or unsubstituted alkyl, or together form a covalent bond;

$R_5$ is hydrogen or substituted or unsubstituted alkyl;

$R_6$ and $R_{6a}$ are each independently hydrogen or substituted or unsubstituted alkyl, or together form =O;

$R_7$ is a covalent bond, alkylene, azaalkyl, or azaaraalkyl or =NR$_{20}$ where $R_{20}$ is 3,5-bis(tri-fluoromethyl)benzyl or —CH$_2$X—R$^1$ or —YR$^1$ where Y is an aryl or heteroaryl group;

$R_8$ and $R_{8a}$ are each independently hydrogen or substituted or unsubstituted alkyl or together form =O;

$R_9$ and $R_{10}$ are each independently hydrogen, or substituted or unsubstituted alkyl and $R_9$ may be —CH$_2$CH$_2$COOR$^2$ where $R^2$ is an alkyl group that may optionally substituted with one or more fluorine atoms;

each of $R_1$-$R_{10}$, when substituted, is substituted with one or more substituents each independently selected from Q, where Q is alkyl, haloalkyl, halo, photosensitizereudohalo, or —COOR$_b$ where $R_b$ is hydrogen, alkyl, alkenyl, alkynyl, cycloalkyl, aryl, heteroaryl, araalkyl, or OR$_c$ where $R_c$ is hydrogen, alkyl, alkenyl, alkynyl, cycloalkyl, or aryl or CONR$_d$R$_e$ where $R_d$ and $R_e$ are each independently hydrogen, alkyl, alkenyl, alkynyl, cycloalkyl, or aryl, or NR$_f$R$_g$ where $R_f$ and $R_g$ are each independently hydrogen, alkyl, alkenyl, alkynyl, cycloalkyl, or aryl, or =NR$_h$ where $R_h$ is hydrogen, alkyl, alkenyl, alkynyl, cycloalkyl, or aryl, or is an amino acid residue;

each Q is independently unsubstituted or is substituted with one or more substituents each independently selected from $Q_1$, where $Q_1$ is alkyl, haloalkyl, halo, photosensitizereudohalo, or —COOR$_b$ where $R_b$ is hydrogen, alkyl, alkenyl, alkynyl, cycloalkyl, aryl, heteroaryl, araalkyl, or OR$_c$ where $R_c$ is hydrogen, alkyl, alkenyl, alkynyl, cycloalkyl, or aryl or CONR$_d$R$_e$ where $R_d$ and $R_e$ are each independently hydrogen, alkyl, alkenyl, alkynyl, cycloalkyl, or aryl, or NR$_f$R$_g$ where $R_f$ and $R_g$ are each independently hydrogen, alkyl, alkenyl, alkynyl, cycloalkyl, or aryl, or =NR$_h$ where $R_h$ is hydrogen, alkyl, alkenyl, alkynyl, cycloalkyl, or aryl, or is an amino acid residue.

The photosensitizer may be conjugated with an image enhancing agent prior to incorporation into the nanoparticle, after incorporation into the nanoparticle or the photosensitizer and/or image enhancing agent may chemically bound to the nano particle and/or one or more of the photosensitizer and image enhancing agent may be physically bound to the nanoparticle.

Imaging enhancing agents may be for essentially any imaging process, e.g. Examples of such imaging enhancing agents are discussed in the background of the invention previously discussed and in the list of references incorporated by reference herein as background art.

It is to be understood that other agents may be incorporated into the nanoparticle such as tumor targeting moieties and tumor inhibiting or tumor toxic moieties.

BRIEF DESCRIPTION OF THE SEVERAL VIEWS OF THE DRAWINGS

The file of this patent contains at least one drawing executed in color. Copies of this patent with color drawing(s) will be provided by the Patent and Trademark Office upon request and payment of the necessary fee.

FIG. 19A at B is a fluorescence image using cyanine dye (CD) containing a carboxylic acid group conjugated at the periphery of the PAA NPs and FIG. 19A at C is a fluorescence image using cyanine dye alone. Essentially no tumor uptake is shown.

DETAILED DESCRIPTION OF THE INVENTION

Photosensitizers (photosensitizer) generally fluoresce and their fluorescence properties in vivo has been exploited for the detection of early-stage cancers in the lung, bladder and other sites. For treatment of early disease or for deep seated tumors the fluorescence can be used to guide the activating light. However, photosensitizers are not optimal fluorophores for tumor detection for several reasons: (i) They have low fluorescence quantum yields (especially the long wavelength photosensitizers related to bacteriochlorins). Efficient photosensitizers tend to have lower fluorescence efficiency (quantum yield) than compounds designed to be fluorophores, such as cyanine dyes because the excited singlet state energy emitted as fluorescence is instead transferred to the triplet state and then to molecular oxygen. (ii) They have small Stokes shifts. Porphyrin-based photosensitizer have a relatively small difference between the long wavelength absorption band and the fluorescence wavelength (Stokes shift), which makes it technically difficult to separate the fluorescence from the excitation wavelength. (iii) Most photosensitizers have relatively short fluorescent wavelengths, <800 nm, which are not optimal for detection deep in tissues.

Figure 1A:
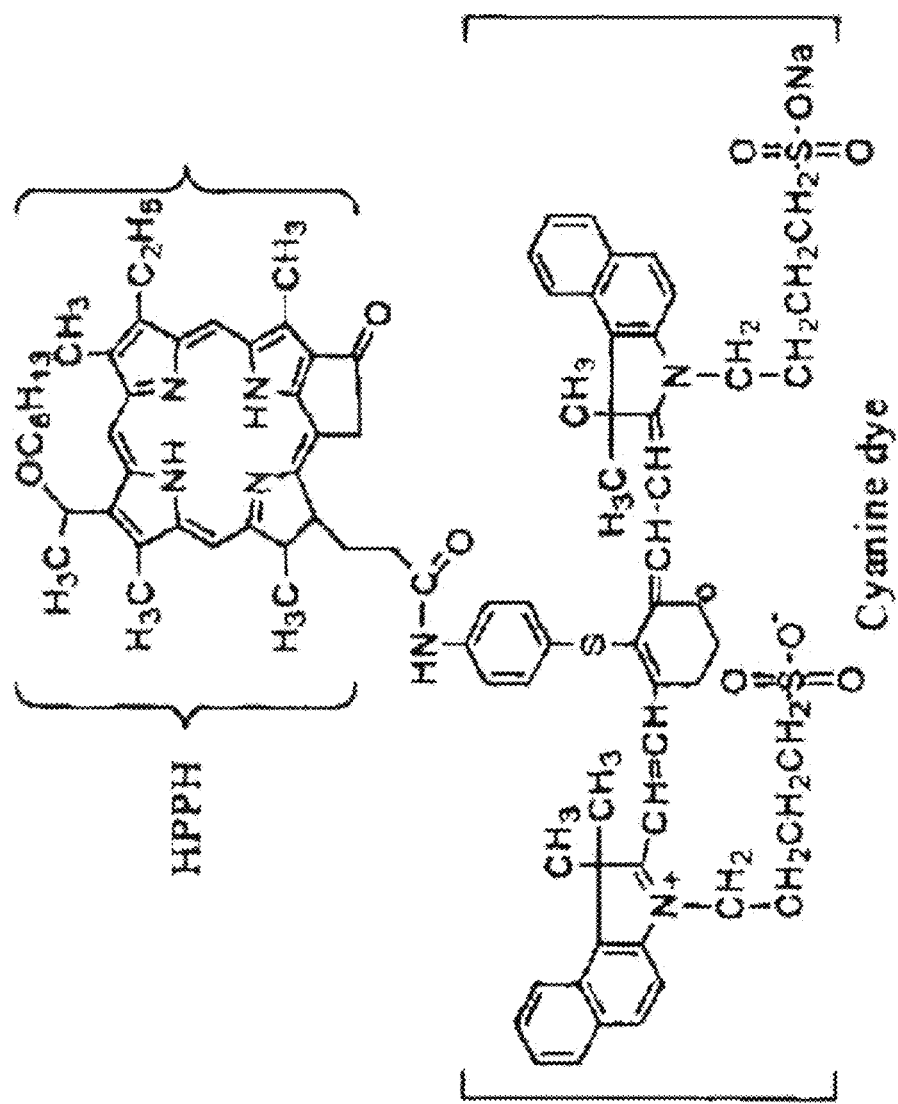
FIG. 1A shows the structural formula of HPPH-CD (cyanine dye) conjugate used as a photosensitizer and imaging agent.
Figure 1B:
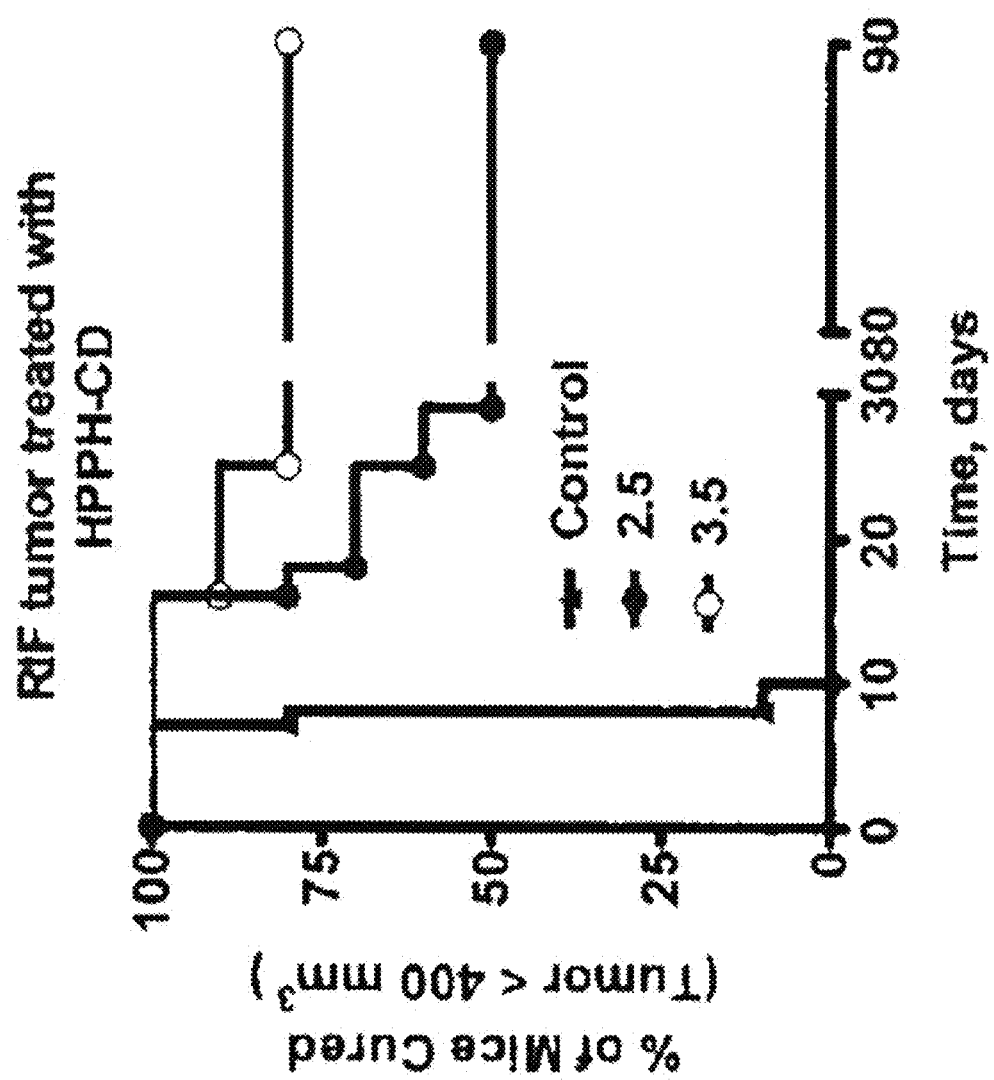
FIG. 1B is a graph showing in vivo photosensitizing efficacy of HPPH-CD conjugate 1 in C3H mice bearing RIF tumors (10 mice/group) at variable drug doses. The tumors were exposed to light (135 J/cm2/75 mW/cm2) at 24 h post-injection.
Figure 1C:
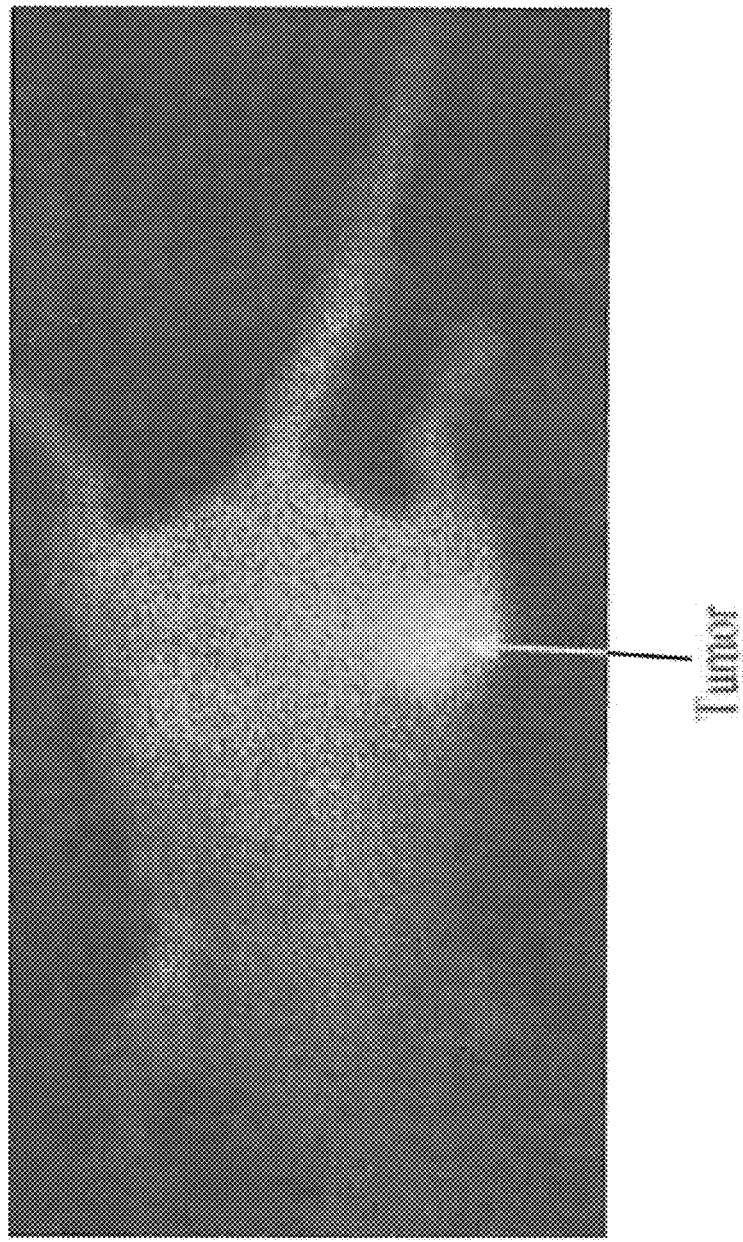
FIG. 1C shows a scanned image showing localization of the conjugate 1 in a live mouse 24 h after injection (drug dose 0.3 µmole/kg). (Without PAA NP0)

We have previously shown that certain tumor-avid photosensitizer(s) (e.g., HPPH) conjugated with NIR absorbing fluorophore(s) (non-tumor specific cyanine dyes) can be used as bifunctional agents for tumor-imaging by fluorescence and phototherapy (PDT). Here, HPPH was used as a vehicle to deliver the imaging agent to tumor. The limitation of this approach was that the conjugate exhibited significantly different dose requirements for the two modalities. The imaging dose was approximately 10-fold lower than the photherapeutic dose (FIGS. 1B and 1C), which could be due to a part of the singlet oxygen (a key cytotoxic agent responsible for the destruction of the tumors) produced on exciting the photosensitizer being quenched by the fluorophore leading to its photo-destruction. Exposing the tumor at 780 nm (excitation wavelength for the cyanine dye) produced in vivo emission at 860 nm and, as expected, no significant photobleaching of the fluorophore (CD) or the photosensitizer (HPPH) was observed.

Figure 2:
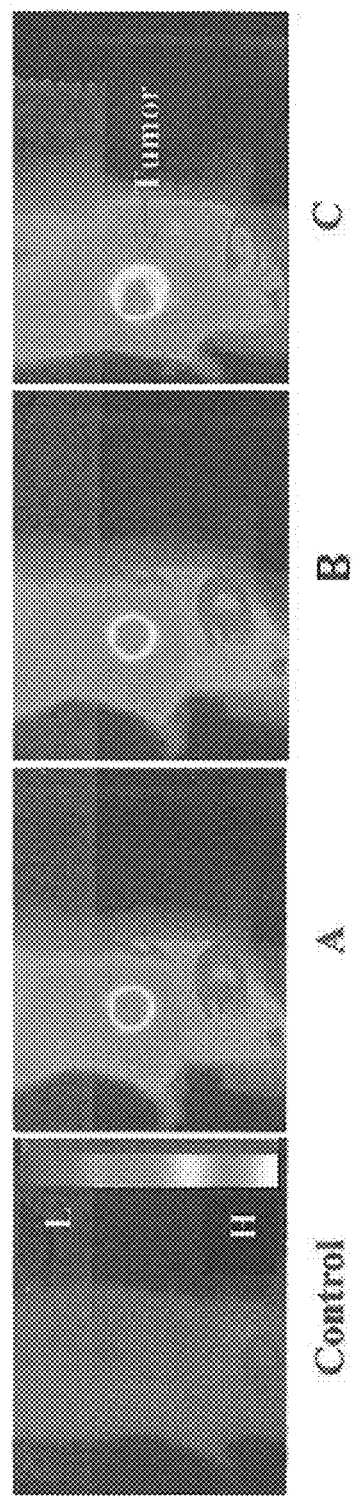
FIG. 2 shows whole body images of BALB/c mice bearing Colon26 tumors with PAA NPs formulations (HPPH and cyanine dye (CD) were post-loaded in 2 to 1 ratio). The CD concentration was kept constant (0.3 µmol/kg) at the images were obtained at variable time points. A=24 h, B=48 h and C=72 h post injection (λex: 785 nm; λEm: 830 nm). L=Low and H=High.
Figure 3:
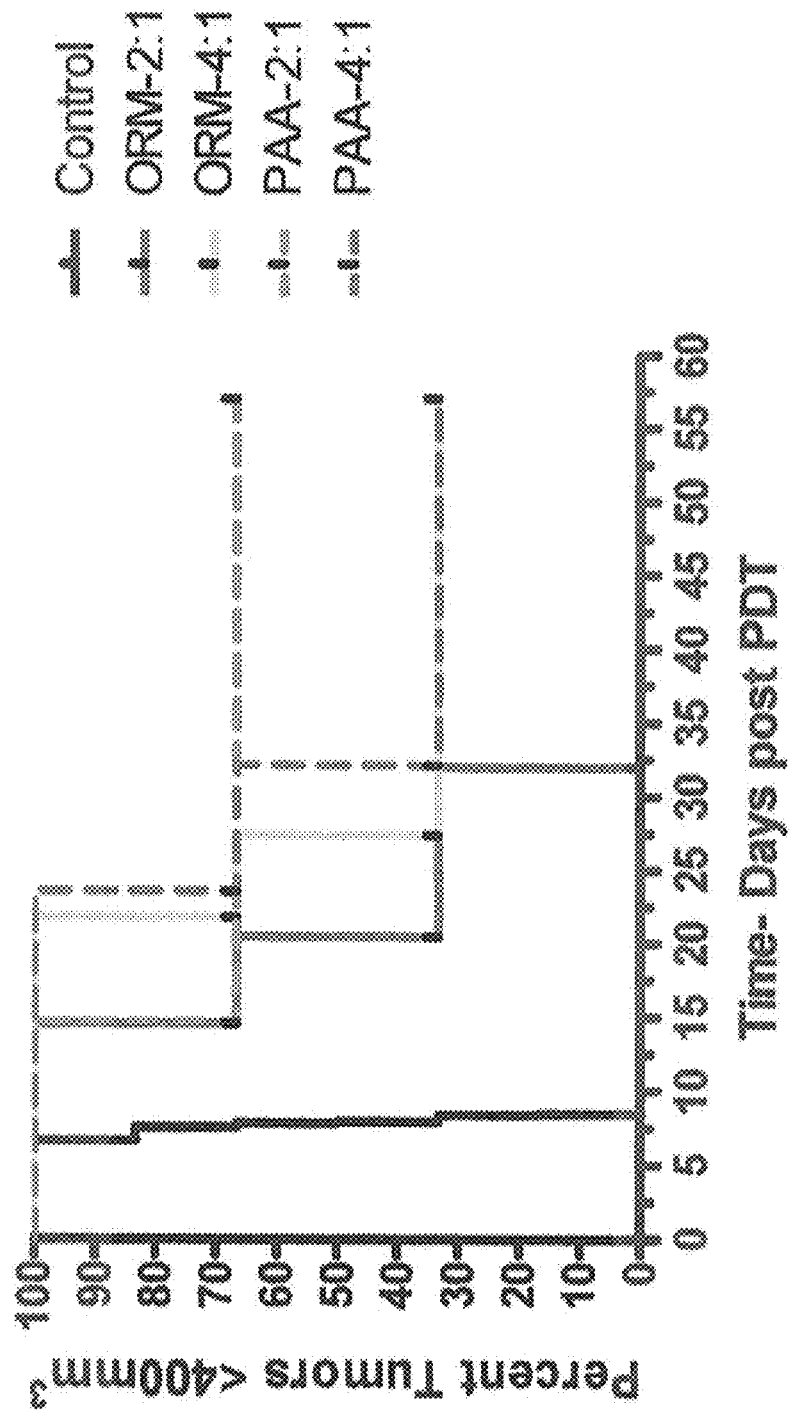
FIG. 3 is a graph showing in vivo PDT efficacy of HPPH and CD post loaded in a ratio of 2:1 and 4:1 in PAA and ORMOSIL NPs. Note: HPPH dose: 0.47 μmol/kg in PAA NPs and 0.78 μmol/kg in ORMOSIL NPs.
Figure 4:
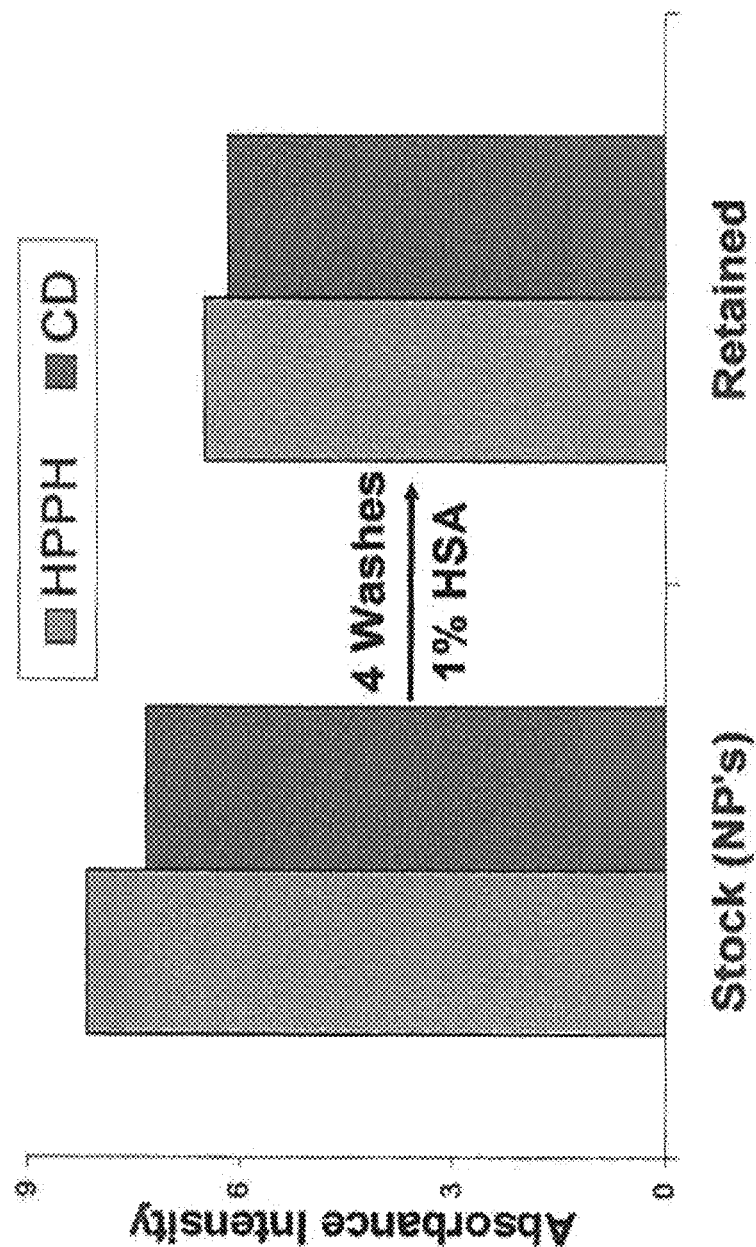
FIG. 4. Slow release of HPPH and CD from PAA NPs (post loaded in 2:1 ratio) after several washes with 1% HSA.
Figure 5A:
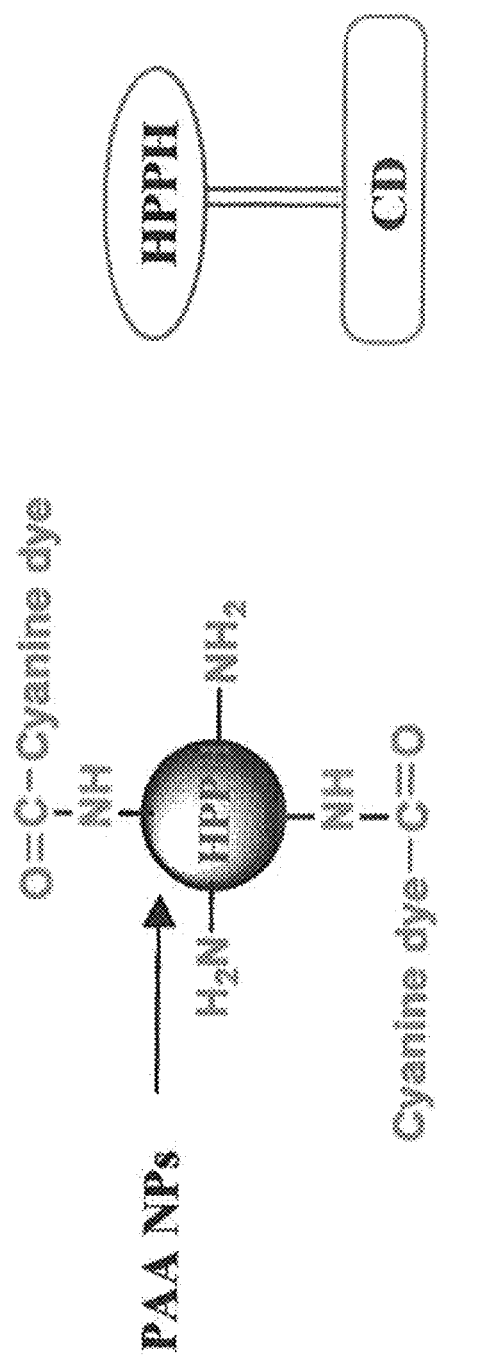
FIG. 5A is a diagram showing structure of PAA nanoparticles (PAA NP's)
Figure 5B:
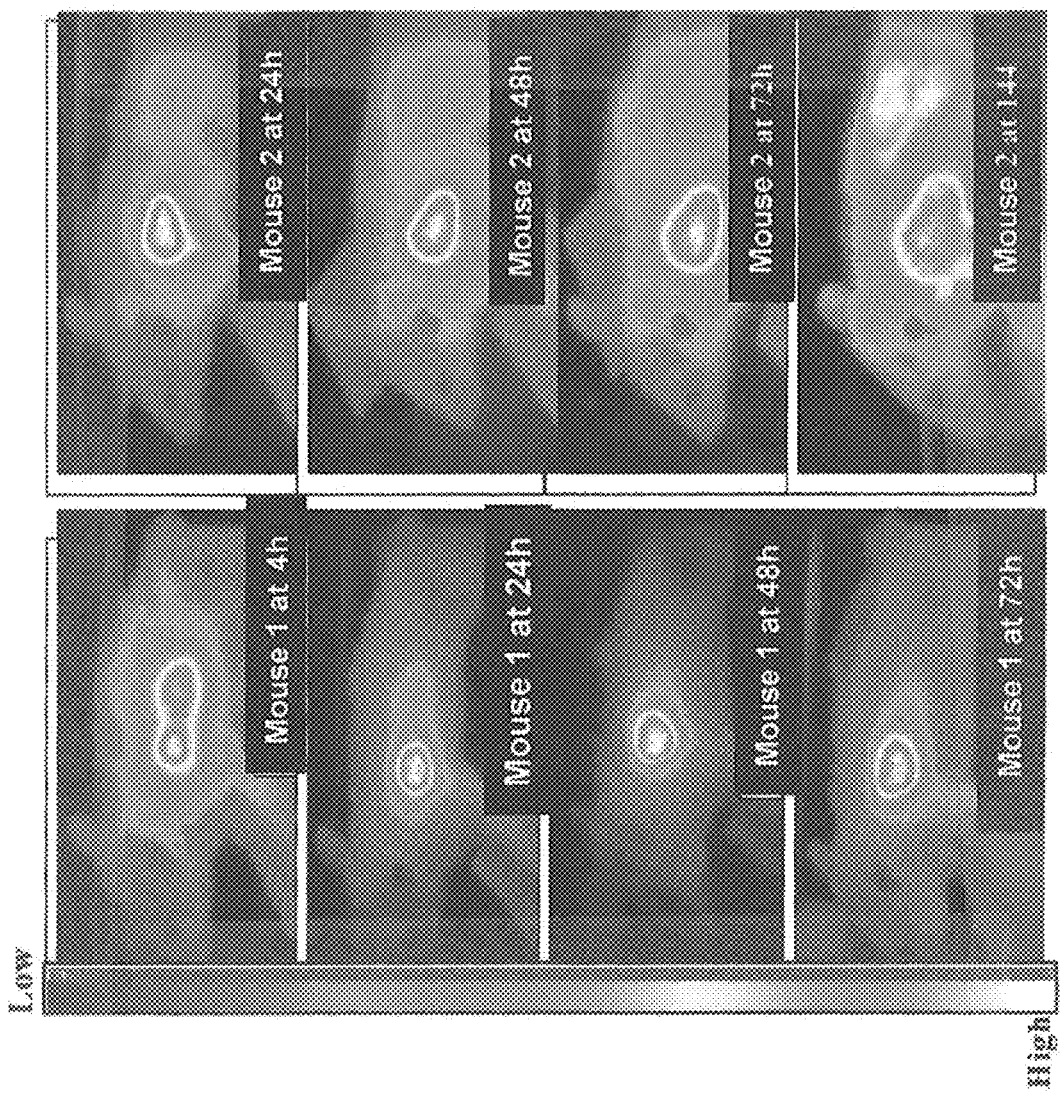
FIG. 5B shows. comparative in vivo imaging at variable time points of BALB/c mice bearing Colon26 tumors with HPPH-CD conjugate 1 and CD-conjugated with PAA NPs/post-loaded with HPPH. The NPs were more tumor specific. (Mouse 1)

For investigating the utility of PAA nanoparticles three different approaches were used. First HPPH and the cyanine dye (fluorophore) were post-loaded in variable ratios (HPPH to CD: 1:1; 2:1; 3:1 and 4:1 molar concentrations). In brief, HPPH was postloaded to PAA nanoparticles first. Free HPPH was removed by spin filtration and then cyanine dye was postloaded. It was spin-filtered again, washed several times with 1% bovine calf serum and the concentration was measured. The 2:1 formulations produce the best tumor imaging and long-term tumor cure in BALB/c mice bearing Colon26 tumors. This formulation contained in a single dose the therapeutic dose of HPPH (0.47 µmol/kg) and the imaging dose of Cyanine dye (0.27 mol/kg), which were similar to the components used alone for tumor imaging and therapy, but with much more tumor selectivity (skin to tumor ratio of HPPH was 4:1 instead of 2:1 without nanoparticles). Under similar treatment parameters the Ormosil nanoparticles showed a significantly reduced response (imaging and PDT, not shown). The stability of the drugs in PAA nanoparticle was established by repeated washing with aqueous bovine calf serum through Amicon centrifugal filter units with a 100 KDa or larger cut off membrane and drug in the filtrate was measured spectrophotometrically. The comparative in vivo PDT efficacy of the ORMOSIL and PAA formulations, their tumor imaging potential and stability (in vitro release kinetics) is shown in FIGS. 2-4, which clearly illustrate the advantages of PAA nanoparticles in reducing the therapeutic dose by almost 8-fold without diminishing the tumor-imaging potential and also avoiding the Tween-80 formulation required for the HPPH-CD conjugate 1. In the $2^{nd}$ approach the HPPH CD conjugate 1 was post-loaded to PAA nanoparticles, which certainly enhanced the tumorimaging, but the therapeutic dose was still 10-fold higher (similar to the HPPH CD conjugate, FIG. 5B). In the 3rd approach the cyanine dye was conjugated peripherally to the PAA nanoparticles first and then HPPH was post loaded. Again, compared to HPPH-CD conjugate 1, the PAA formulation showed enhanced tumor-specificity (imaging) (FIG. 5B).

Effect of Nanoparticles on Tumor Selectivity

A photosensitizer (photosensitizer) with increased selectivity and longer wavelength could be a more suitable candidate for brain and deeply seated tumors (especially breast, brain and lung). The evolution of light sources and delivery systems is also critical to the progression of photodynamic therapy (PDT) in the medical field. Two different techniques: interstitial and intracavitary light delivery have been used for treatment of brain tumors. Powers using interstitial PDT on patients with recurrent brain tumors showed that the majority of patients had tumor recurrence within two months of treatment. However, it was later observed that treatment failures appeared to occur outside the region of the effective light treatment. Chang et al reported an effective radius of tumor cell kill in 22 glioma patients of 8 mm compared with the 1.5 cm depth of necrosis noted by Pierria with the intracavitary illumination method. It is believed that tumor resection is important so that the numbers of tumor cells remaining to treat are minimized. With stereotactic implantation of fibers for interstitial PDT there is no cavity to accommodate swelling and a considerable volume of necrotic tumor which causes cerebral edema. However, cerebral edema can be readily controlled with steroid therapy. Compared to chemotherapy and radiotherapy, patients with brain tumors treated with PDT have definitely shown long-term survival, whereas glioma patients treated with adjuvant chemotherapy or radiotherapy do not seem to show additional benefits. On the basis of our preliminary data, the $\alpha v \beta 3$ targeted nanoparticles may improve tumor-selectivity and PDT outcome.

Figure 6:
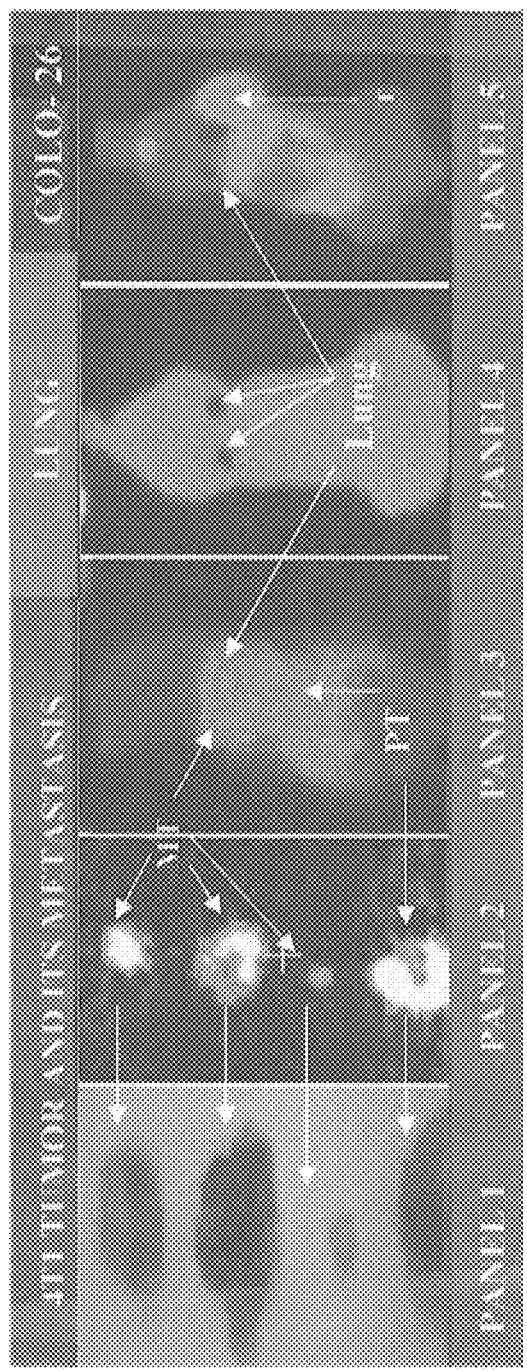
FIG. 6 shows a series of scans wherein Panel 1 (4T1 tumors): Primary (PT) and metastasized tumors (MT) dissected and Panel 2 (4T1 tumors): PET imaging of the dissected primary and metastasized tumors. Panel 3 (BALB/C mouse bearing 4T1 tumor): Whole body PET imaging. The tumor metastasis in lung was clearly observed. Panel 4: The position of the lung is shown by the transmission scan using 57Co source in mice with no lung metastasis. Panel 5: (BALB/C mouse bearing Colo-26 (non-metastatic tumor): Whole body imaging by PET. A high accumulation of the 124I-photosensitizer in tumor is clearly observed without any significant accumulation in lungs (injected dose: 100 μCi). T=Tumor, PT=Primary tumor; MT=Metastatic tumor.
Figure 7:
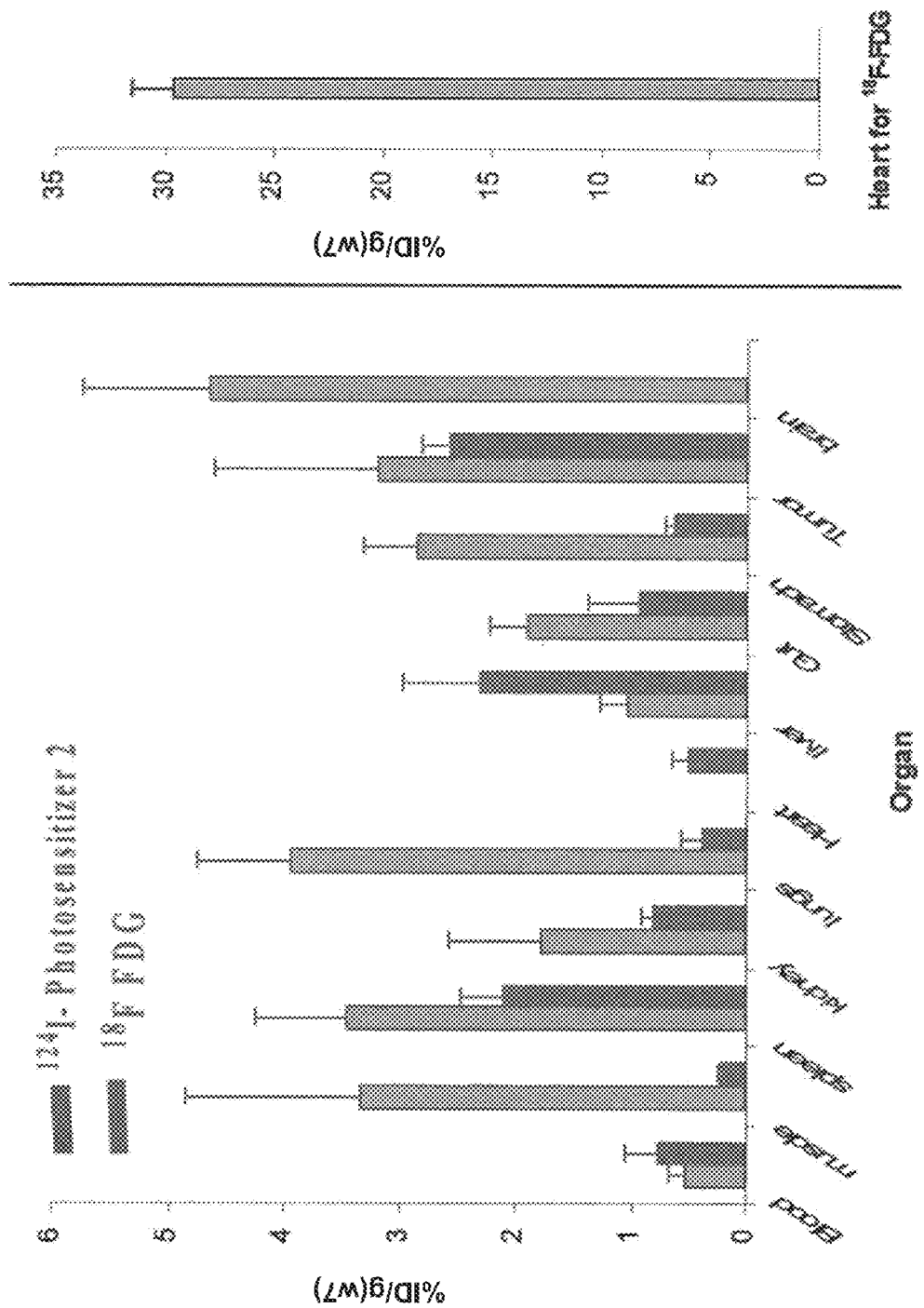
FIG. 7. In vivo biodistribution of 18F-FDG (100 μCi, half-life 2 h) at 110 min and 124I-PS 2 (100 μCi, half-life 4.2 d) at 48 h in BALB/c mice bearing Colon 26 tumor (3 mice/group). Tumor-uptake was similar for both agents. However, the higher uptake of FDG over 124I-PS 2 in normal organs is clearly evident.
Figure 8A:
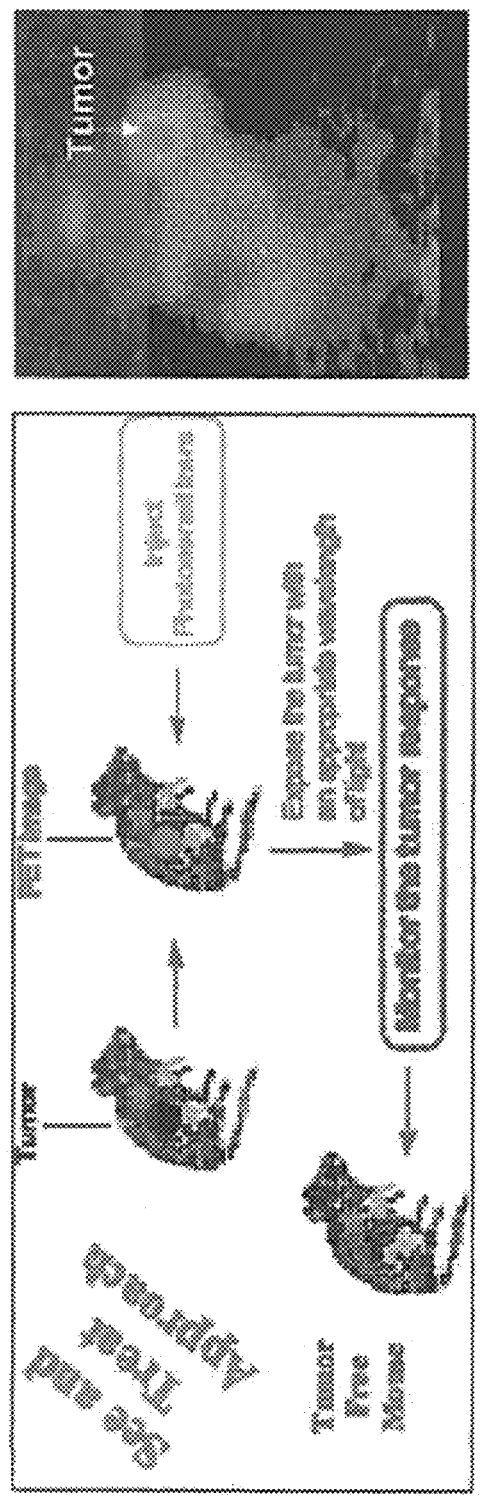
FIG. 8A shows in vivo comparative in vivo PET imaging (72 h post injection) and biodistribution (24 h, 48 h and 72 h postinjection) of 124I-labeled photosensitizer 2 without PAA nanoparticles in BALB/c mice bearing Colon26 tumors (see the text). (Biodistribution of PET imaging agent 2: No PAA, with PAA).
Figure 8B:
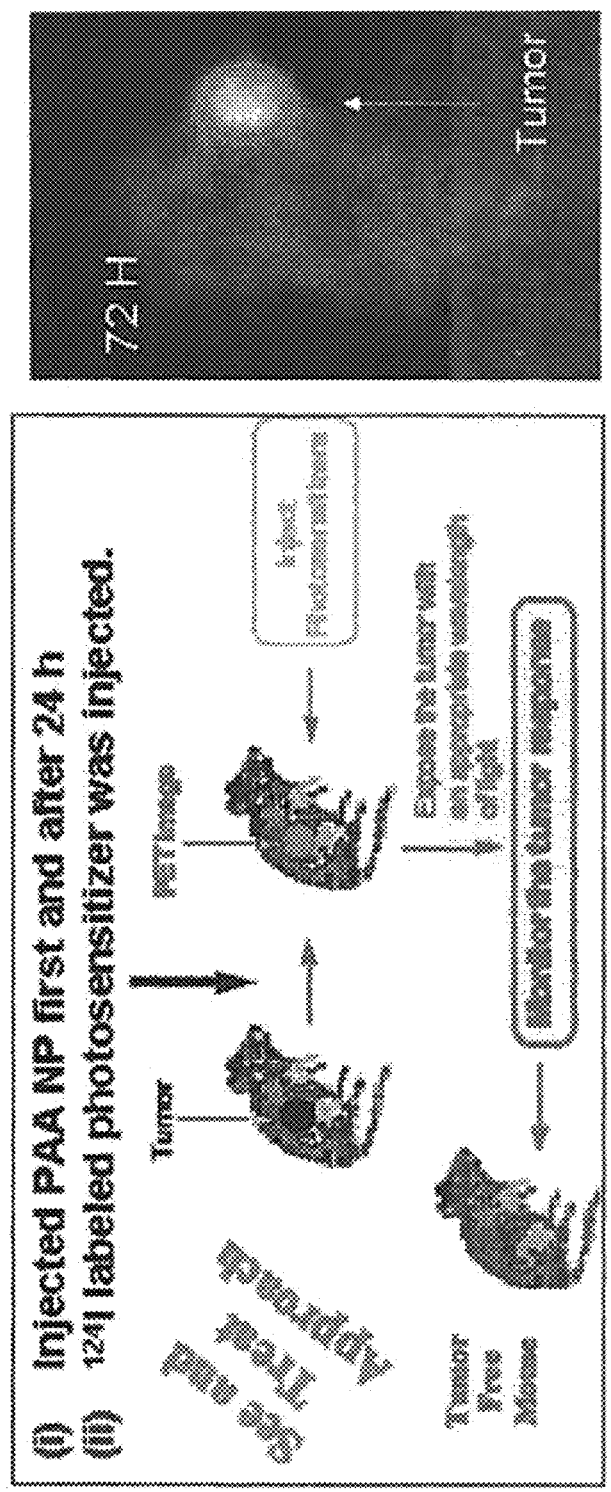
FIG. 8B shows in vivo comparative in vivo PET imaging (72 h post injection) and biodistribution (24 h, 48 h and 72 h postinjection) of 124I-labeled photosensitizer 2 with PAA nanoparticles in BALB/c mice bearing Colon26 tumors (see the text). (Biodistribution of PET imaging agent 2: No PAA, with PAA).
Figure 8C:
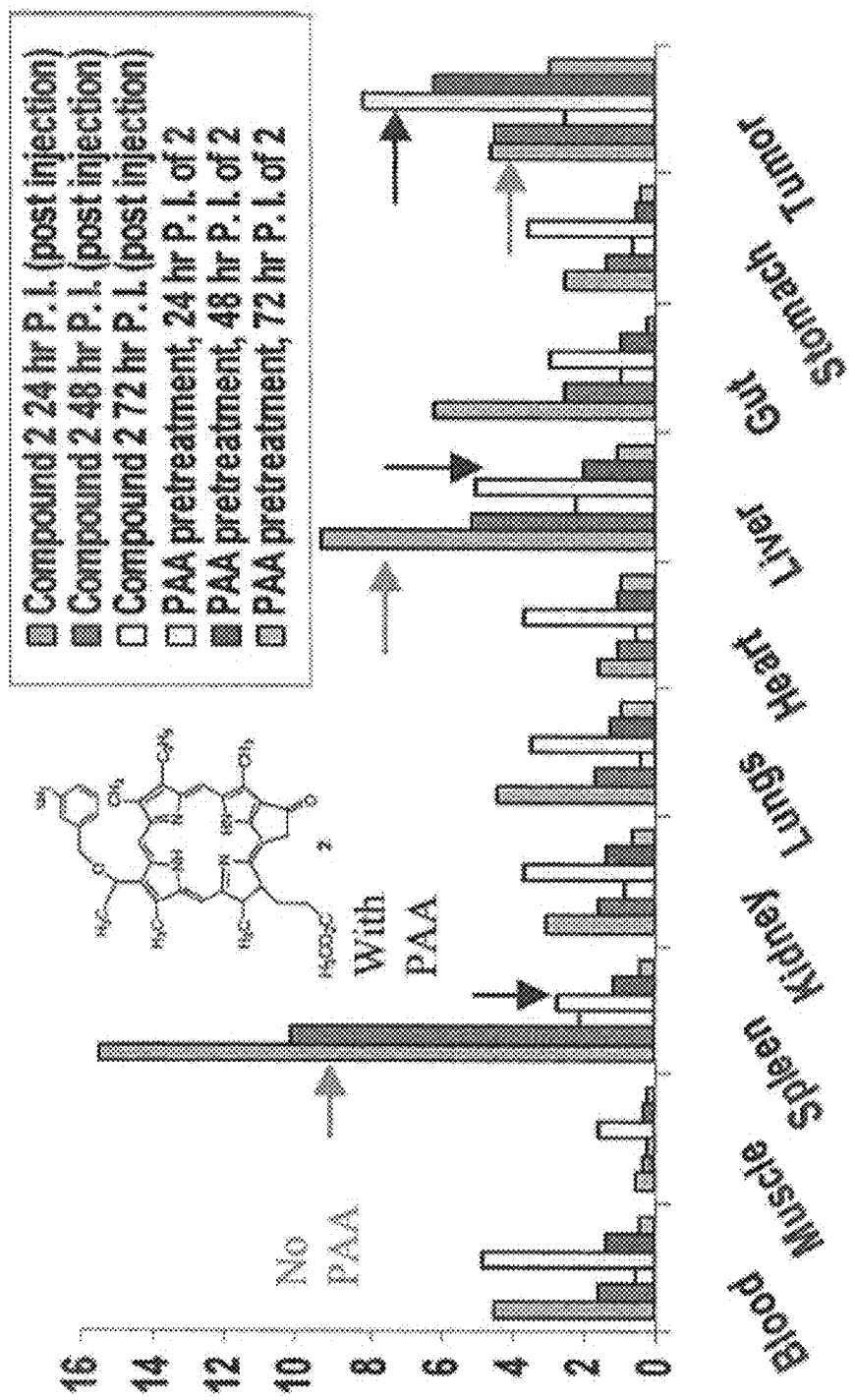
FIG. 8C shows biodistribution of PET imaging agent 2, no PAA and with PAA.

PET Imaging and PDT: PAA Nanoparticles Decreased the Liver Uptake of the 124I-Photosensitizer (PET Imaging Agent) and Enhanced the Tumor-Specificity Our initial investigation with an 124I-labeled photosensitizer 2 indicates its in vivo PDT efficacy and capability of detecting tumors104-106 (RIF, Colon26, U87, GL261, pancreatic tumor xenograft) and tumor metastases (BALB/c mice bearing orthotopic 4T1 (breast tumors) (FIG. 6). Interestingly, compared to 18F FDG photosensitizer 2 showed enhanced contrast in most of the tumors including those where 18F FDG-PET provides limited imaging potential (e.g., brain, lung and pancreatic tumors). See FIG. 7 for comparative biodistribution. This is the first report showing the utility of porphyrin-based compounds as a "BIFUNCTIONAL AGENT" for imaging breast tumor and tumor metastasis. Similar to most nanoparticles, PAA nanoparticles accumulate in liver and spleen. Their clearance rate from most organs is significantly faster than Ormosil nanoparticle and they do not show long-term organ toxicity. Even tumor-avid porphyrinbased photosensitizer exhibit high uptake in liver and spleen, but are non-toxic until exposed to light. The photosensitizer clear from the system quickly (days) without organ toxicity. However, radioactive photosensitizer such as the 124I-labeled analog 2 (superior to 18F-FDG in PET-imaging of lung, brain, breast and pancreas tumors) with a T½ of 4.2 days could cause radiation damage to normal organs. Based on the observation of high uptake of PAA nanoparticles in liver and spleen (below) we postulated that saturating the organs with the non-toxic PAA nanoparticles before injecting the PET agent might reduce uptake and radiation damage by 124I-imaging agent. For proof-of principle blank PAA nanoparticles were first injected (i.v.) into mice bearing Colon26 tumors followed 24 h later by i.v. 124I-analog (100-50 µCi). The mice were imaged at 24, 48 and 72 h post injection and biodistribution studies were performed at each time point summarized in FIG. 8A-8C (only 72 h images shown).

The presence of PAA nanoparticles made a remarkable difference in tumor contrast with brain, lung and pancreatic tumors). See FIG. 7 for comparative biodistribution.

Figure 9:
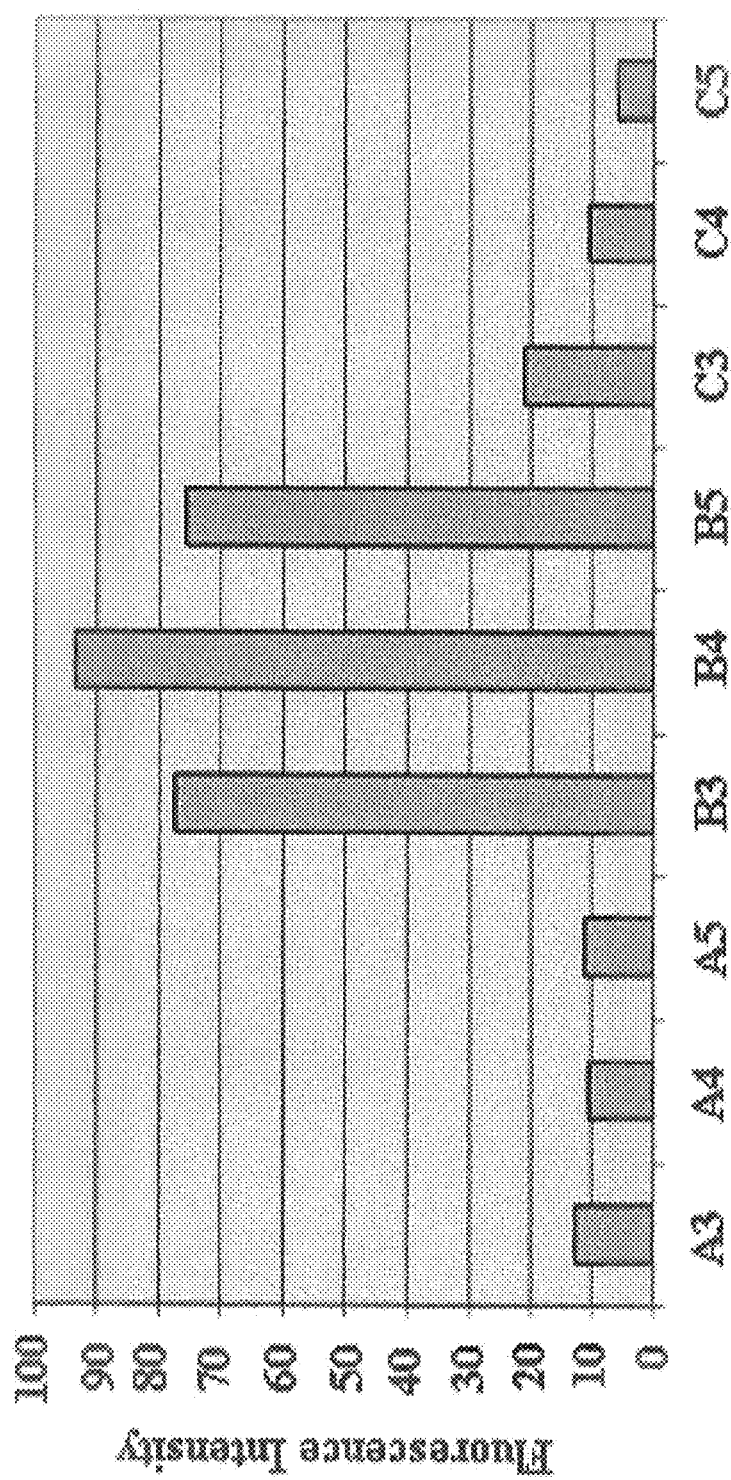
FIG. 9. Fluorescence intensity of cells targeted by F3-targeted (A series), F3-Cys targeted (B series) and nontargeted NPs (F series) in nucleolin rich MDA-MB-435 cell lines.

PAA Nanoparticles can be Targeted to Nucleolin with F3-Cys:

F3-targeted nanoparticles were prepared using two kinds of F3 peptides: F3 peptide conjugated to nanoparticle via one of the 8 lysines available in its sequence and F3-Cys peptide conjugated to nanoparticle via cysteine. Cysteine capped nanoparticles served as non-targeted control. Three 25 mg batches of each type of nanoparticle contained: 2.6, 5.1 and 7.7 mg F3, (A3-A5) respectively; 2.7, 5.3 and 8 mg F3-Cys (B3-B5) respectively, and 0.29, 0.58 and 0.87 mg Cys (C3-C5) respectively. The fluorescence intensity from PAA nanoparticle incubated in vitro with nucleolin positive MDA-MB-435 cells is shown in FIG. 9. The F3-Cys conjugated nanoparticles show considerably higher binding efficiency than non-targeted nanoparticles, while F3 conjugated nanoparticles do not. Conjugation via a cysteine link preserves the specificity of F3 peptide for nucleolin. In addition excess cysteine on the nanoparticles helphotosensitizer to minimize the non-specific binding. Additional experiments (not shown) suggested that the amount of F3-Cys peptide (5.3 mg/25 mg nanoparticle) used for B4 nanoparticles was optimal.

Optical properties of post-loaded PAA nanoparticles. The absorption spectrum of PAA nanoparticles post-loaded with both HPPH and cyanine dye (even at 0.5 mg/ml), clearly shows characteristic signatures for both the photosensitizer and dye, without aggregation-induced broadening, while the fluorescence spectrum shows strong signals from both components.

Figure 11:
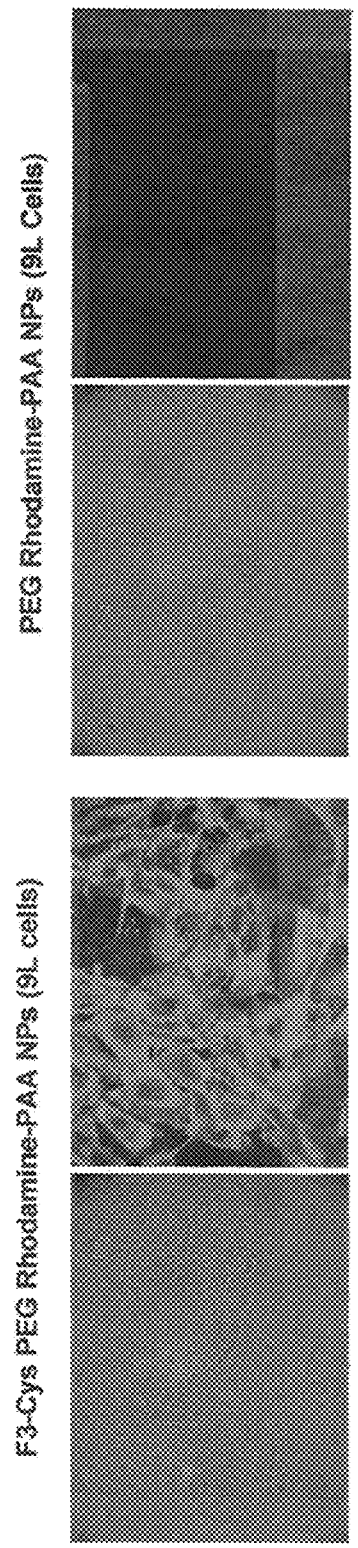
FIG. 11. Confocal images showing the target-specificity of F3-Cys peptide in 9L Glioma tumor cells. Left: F3-Cys PEG Rhodamine-PAA NPs (9L cells). Right: PEG Rhodamine-PAA NPs (9L Cells)

HPPH Conjugated PAA Nanoparticles with F3-Cys Peptide at the Outer Surface Show Targeted Specificity:

F3-mediated specificity is retained in the presence of conjugated HPPH. F3 targeted nanoparticles did targeted nanoparticles did not, indicating that F3-mediated specificity is retained in the presence of conjugated HPPH. F3 targeted nanoparticles did not accumulate in the nucleus. On activation of cells with light at 660 nm only F3-targeted nanoparticle caused cell kill (FIG. 11). Cell internalization of F3-targeted nanoparticles was confirmed by fluorescence confocal microscopy.

Figure 10:
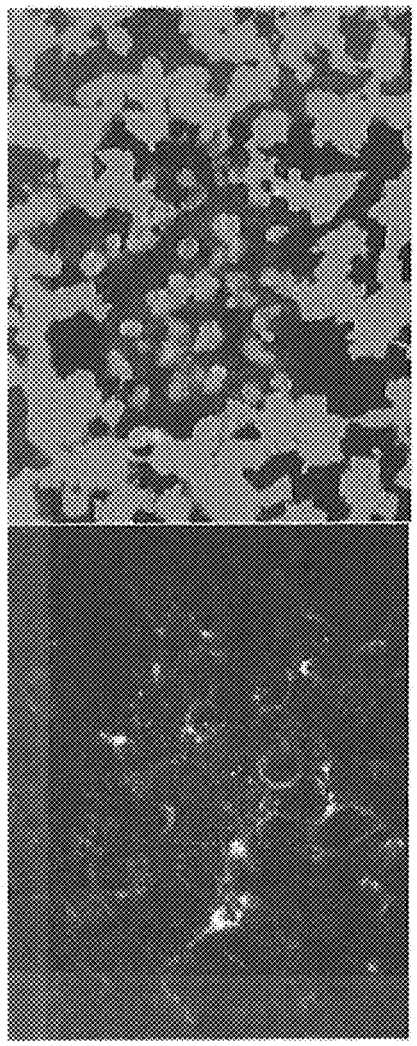
FIG. 10. Fluorescence (left) & Live/dead cell assay (right) of HPPH conjugated PAA NPs + or − F3-Cys peptide incubated for 15 min with MDA-MB-435 cells.
Figure 10:
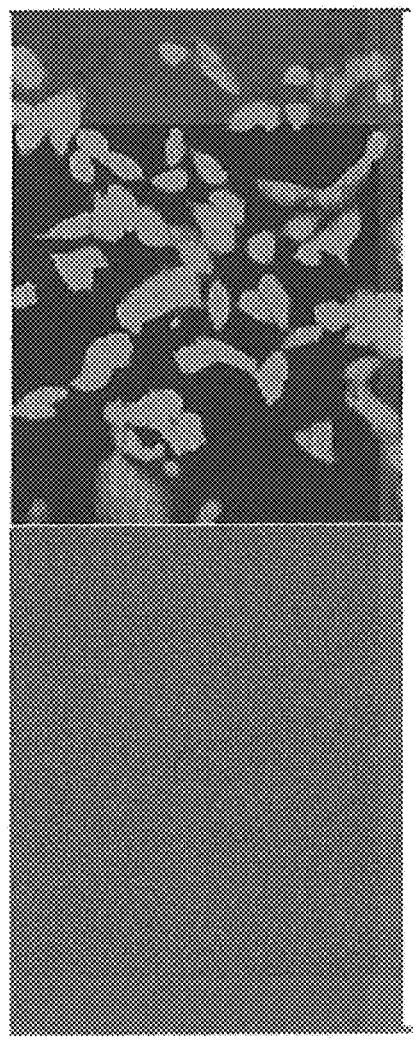

HPPH Conjugated PAA Nanoparticles with F3-Cys Peptide at the Outer Surface Show Targeted Specificity:

The specificity of targeted nanoparticles was tested by fluorescent imaging (FIG. 10). F3 targeted HPPH conjugated PAA nanoparticle specifically bound to MDA-MB-435 cells (expressing nucleolin) while non-targeted nanoparticles did not, indicating that F3-mediated specificity is retained in the presence of conjugated HPPH. F3 targeted nanoparticles did not accumulate in the nucleus. On activation of cells with light at 660 nm only F3-targeted nanoparticle caused cell kill (FIG. 11). Cell internalization of F3-targeted nanoparticles was confirmed by fluorescence confocal microscopy.

F3-Cys Shows Target-Specificity in 9L Glioma Cells:

Similar to F3-cys, a pegylated form of F3-Cys PEG on PAA nanoparticles also showed remarkable target-specificity in 9L rat glioma cells which also expresses nucleolin, FIG. 11. (Note: HPPH is replaced with a Rhodamine moiety).

Figure 12:
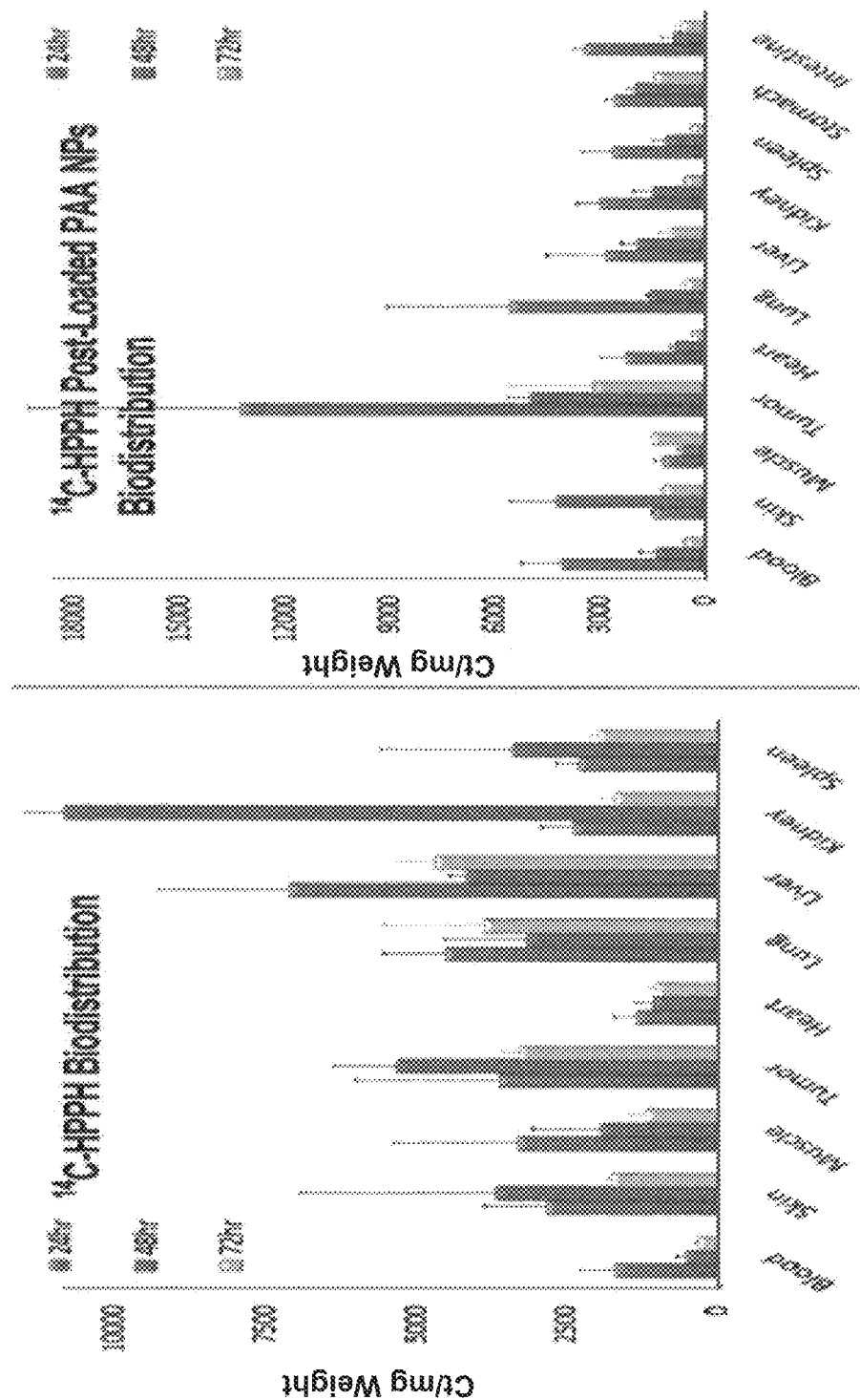
FIG. 12. In vivo biodistribution of $^{14}$C-labeled HPPH, and $^{14}$C-labeled HPPH post-loaded into PAA NPs in BALB/c mice bearing Colon26 tumors. $^{14}$C-labeled PS (3.8 μCi/0.2 mL) were administered to 12 mice/group. At 24, 48, 72 h after. injection, three mice/time-point were sacrificed. The organs of interest were removed and the radioactivity was measured The raw data were converted to counts/gram of tissue.

Biodistribution Studies: PAA Nanoparticle Enhances Tumor Uptake of HPPH:

The biodistbiodistribution of 14C-HPPH and 14C-HPPH post-loaded PAA nanoparticle was performed in BALB/c mice bearing Colon26 tumors at 24, 48 and 72 h post injection (3 mice/time point) and the results are summarized in FIG. 12. As can be seen presence of PAA nanoparticles made a significant increase in tumor uptake with reduced uptake in other organs.

Figure 13A:
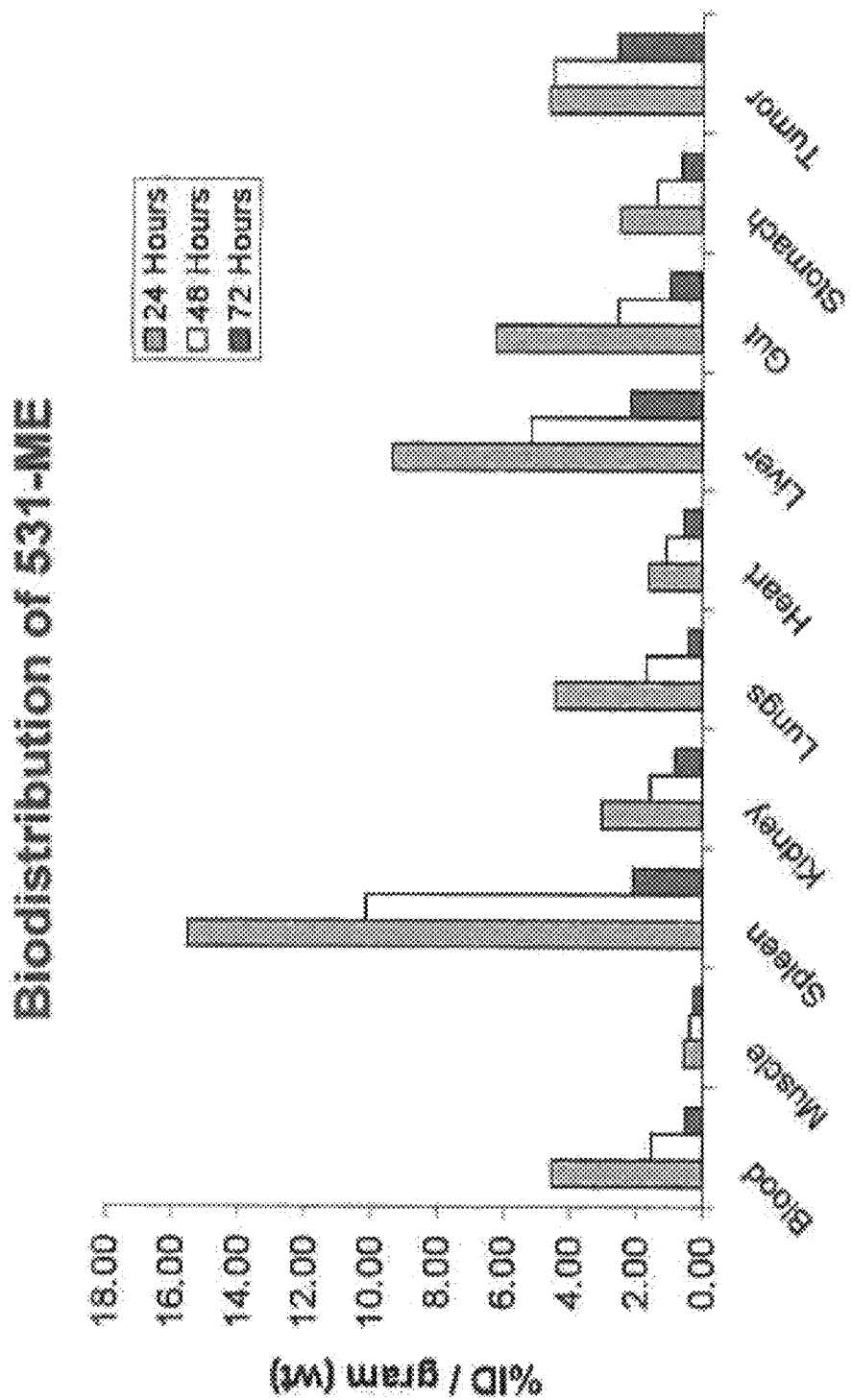
FIG. 13A shows. In vivo biodistribution of iodinated photosensitizer at 24, 48 and 72 h post injection
Figure 13B:
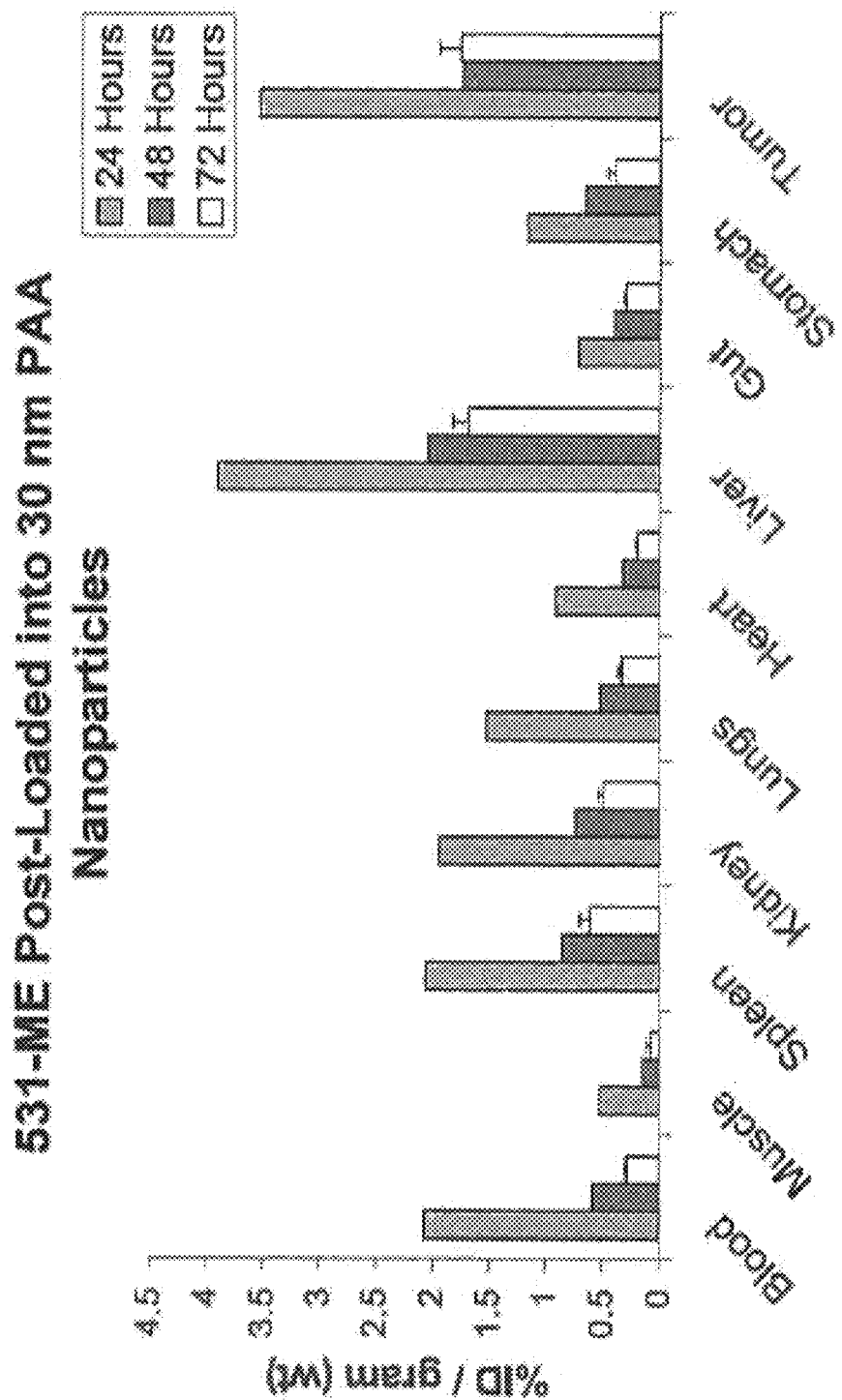
FIG. 13B shows. In vivo biodistribution of iodinated photosensitizer using variable sizes of PAA NPs at 24, 48 and 72 h post injection 531-ME Post-Loaded into 30 nm PAA Nanoparticles.
Figure 13C:
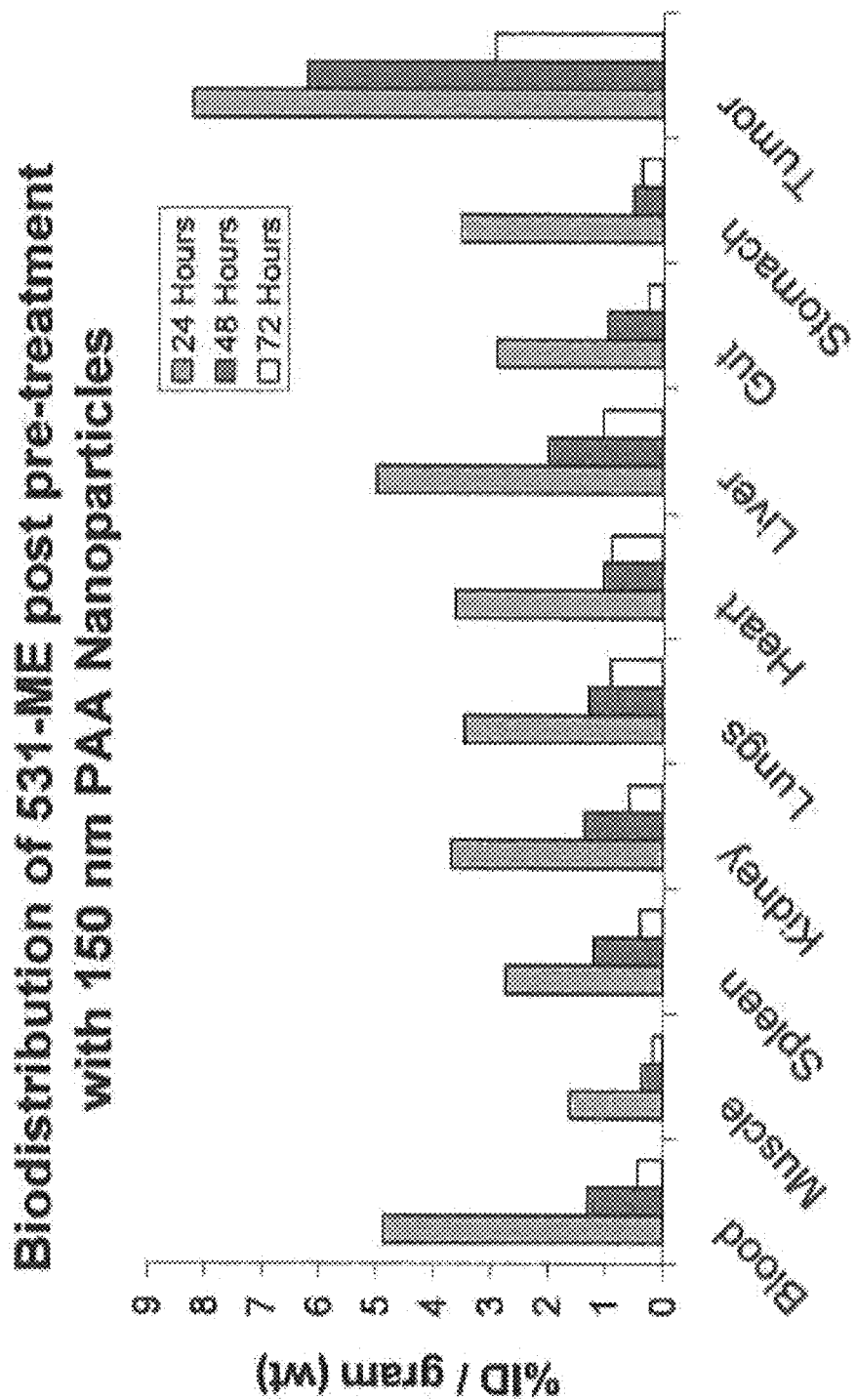
FIG. 13C shows. In vivo biodistribution of iodinated photosensitizer using variable sizes of PAA NPs at 24, 48 and 72 h post injection 531-ME Post-Loaded into 150 nm PAA Nanoparticles.
Figure 14:
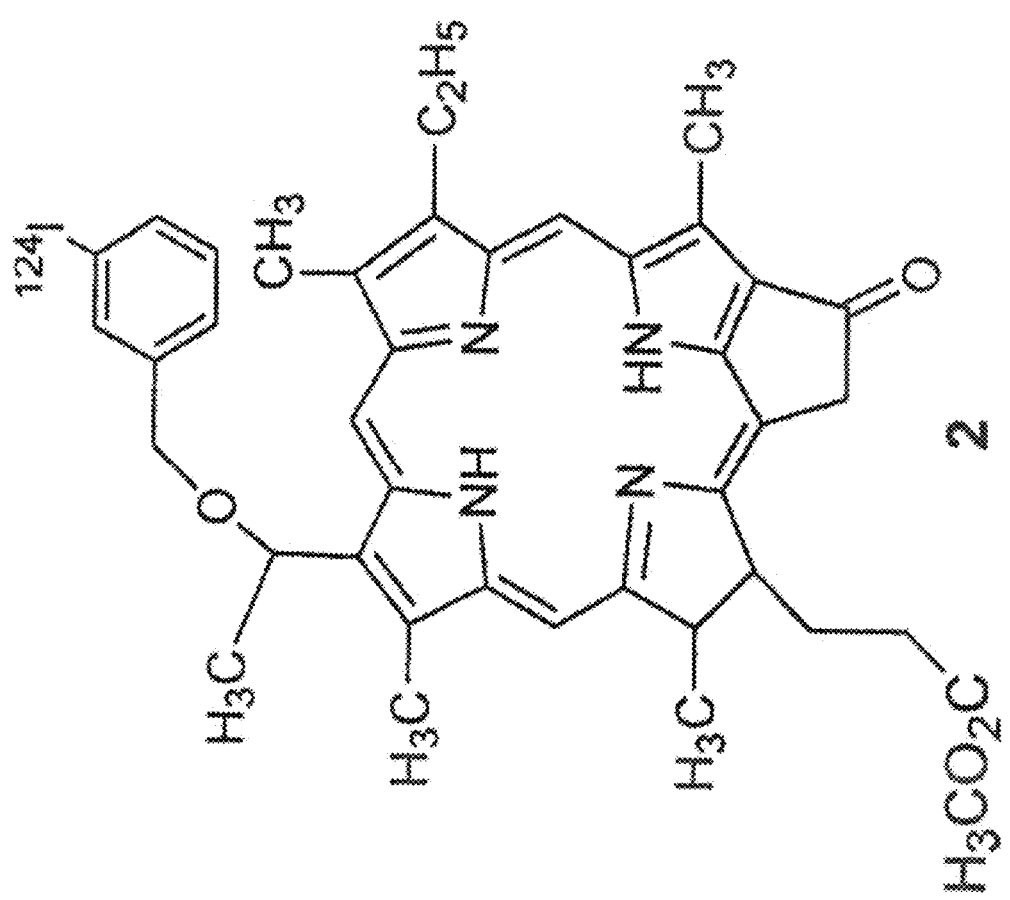
FIG. 14 shows the structural formula of HPPH.
Figure 15:
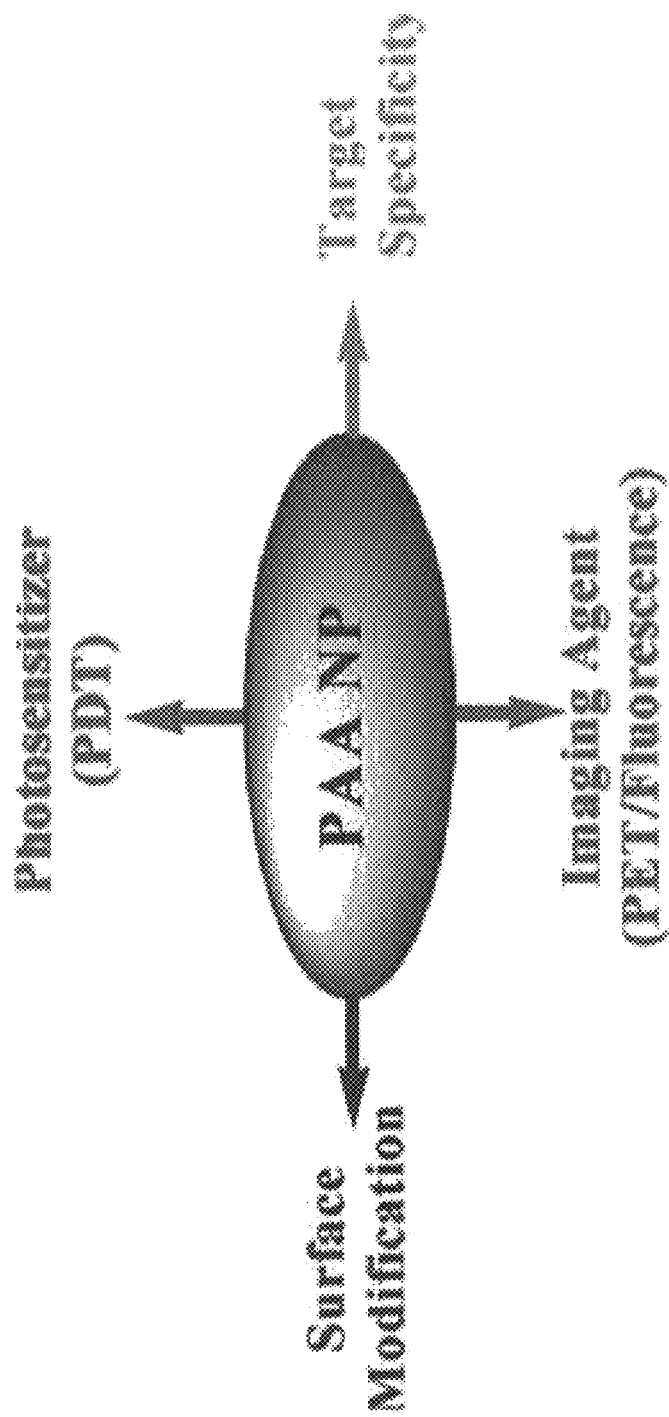
FIG. 15 is a diagram of Multifunctional PAA Nanoparticles.
Figure 16:
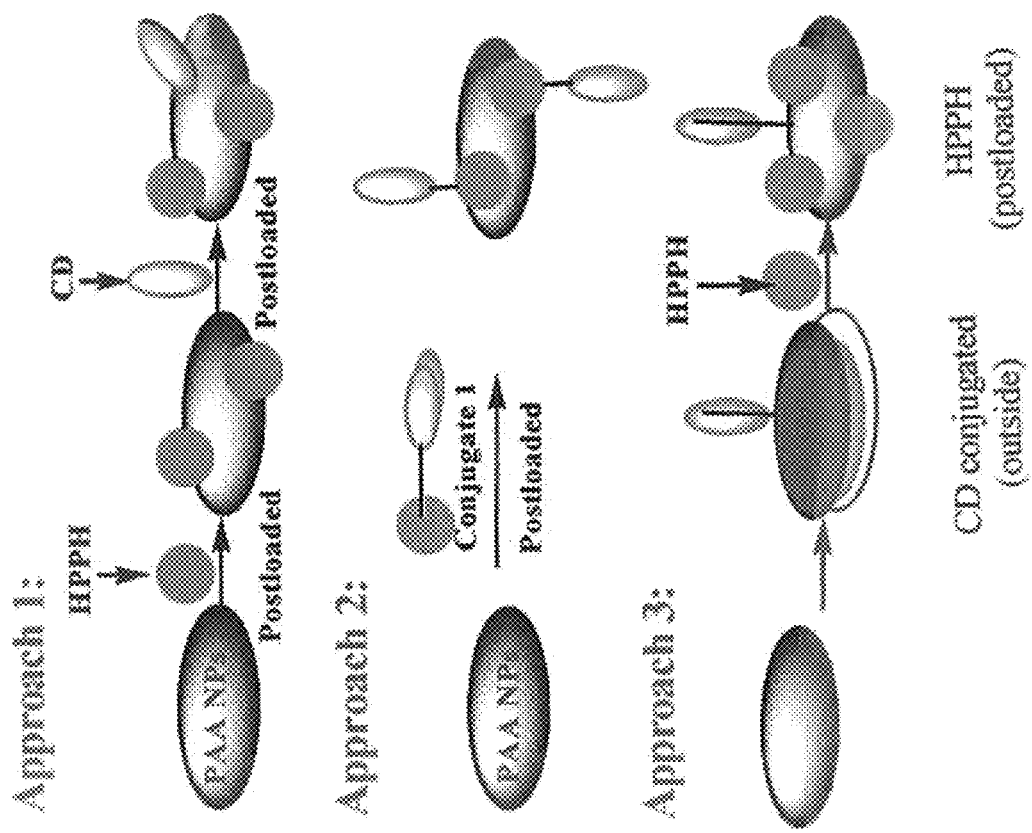
FIG. 16 shows flow diagrams for preparation of postloaded nanoparticles.

Size of PAA Nanoparticles Made Remarkable Difference in Tumor-Enhancement:

The biodistribution of 124I-photosensitizer was investigated using variable sizes of nanoparticles either injecting the nanoparticles first and then administrating the labeled photosensitizer or postloading the labeled photosensitizer to PAA nanoparticles and then perform in vivo biodistribution in mice at 24, 48 and 72 h. The results summarized in FIG. 13A-13C clearly indicate that the size of PAA nanoparticles makes a significant impact in tumor enhancement. Experiments related to in vivo PDT efficacy of these formulations are currently in progress.

This invention shows the utility of porphyrin-based compounds in a "bifunctional agent" for imaging breast tumor and tumor metastasis. Similar to most nanoparticles, PAA nanoparticles accumulate in liver and spleen. Their clearance rate from most organs is significantly faster than Ormosil nanoparticles and they do not show long-term organ toxicity. Even tumor-avid porphyrin based photosensitizers exhibit high uptake in liver and spleen, but are non-toxic until exposed to light. The photosensitizers clear from the system quickly (days) without organ toxicity. However, radioactive photosensitizers such as the 124I-labeled analog 2 (superior to 18F-FDG in PET-imaging of lung, brain, breast and pancreas tumors) with a T½ of 4.2 days could cause radiation damage to normal organs. Based on the observation of high uptake of PAA nanoparticles in liver and spleen (below) we postulated that saturating the organs with the non-toxic PAA nanoparticles before injecting the PET agent might reduce uptake and radiation damage by 124I-imaging agent. For proof-of principle blank PAA nanoparticles were first injected (i.v.) into mice bearing Colon26 tumors followed 24 h later by i.v. 124I-analog (100-150 µCi). The mice were imaged at 24, 48 and 72 h post injection and biodistribution studies were performed at each time point summarized in FIG. 8A-8C (only 72 h images shown).

The presence of PAA nanoparticles makes a remarkable difference in tumor contrast with significantly reduced uptake in spleen and liver and improved tumor-uptake/contrast at 24, 48 and 72 h post injection (3 mice/group Similar studies (tumor-imaging and PDT efficacy) in which the labeled photosensitizer is post-loaded to variable sizes. Similar studies (tumor-imaging and PDT efficacy) in which the labeled photosensitizer is post-loaded to variable sizes PAA nanoparticles are currently in progress.

In more detail, the development of effective multifunctional agents for imaging and PDT by following two approaches is being pursued. In the first approach, 3-(1'-hexyloxyethyl)pyropheophorbide-a [HPPH, a chlorophyll-a derivative (660 nm) currently in Phase I/II clinical trials] was used as a vehicle in delivering the desired fluorescence and nuclear imaging (PET) agents to tumors The second approach was focused on selecting a biocompatible/biodegradable non-toxic nanoplatform, choosing between organically modified silica (ORMOSIL) and polyacrylamide (PAA) nano-platforms for image-guided therapy. In both approaches, HPPH (660 nm) was used as a photosensitizer (PS) and the detailed investigations gave promising results. Among the NPs investigated, the PAA nanoplatform was given preference, due to its biocompatibility and limited toxicity. HPPH may be replaced with 800 nm PDT agents and their biological efficacy compared with and without the nanoparticle formulation. This study is aimed to select the "ideal" candidate for image-guided PDT of brain tumors, with and without surgery.

It is well established that photon migration into tumor tissue is highly dependent on the absorption and scattering properties of tissue components. The near-infrared (NIR) region of the spectrum offers certain advantages for photon penetration. Therefore, efforts are currently underway in various laboratories (including ours) to develop PDT agents with long wavelength absorption, near 800 nm. The availability of inexpensive light emitting diodes (LEDs) in this region will also make PDT more applicable and economical.

Initial results with PAA NPs indicate that multifunctional nanoparticles incorporating both phototherapeutic and imaging agents are uniquely promising in delivering high payloads of these agents to tumors. The success of combined PDT and imaging relies on the development of tumor-avid molecules (EPR effect or target-specific) that are preferentially retained in malignant cells but cleared from surrounding cells and normal tissues.

On the basis of preliminary data, we extrapolated that a PAA nanoplatform containing both NIR therapeutic (800 nm) and imaging agents as separate monomers will help to treat brain cancer patients in combination of Surgery and PDT via image-guided therapy. Tumor-specificity can further be enhanced by targeting the neovasulature and/or $\alpha_v\beta_3$ integrin, known for its over-expression in highly metastatic brain tumors.

This Study was Divided in Following Two Aims:

Aim 1: To investigate the utility of PAA nanoparticles in developing multifunctional platforms by (i) post-loading both the monomeric therapeutic and imaging agents, and (ii) conjugating the fluorescence agent at the periphery of the NPs and post-loading the PET/PDT agent.

Figure 17A:
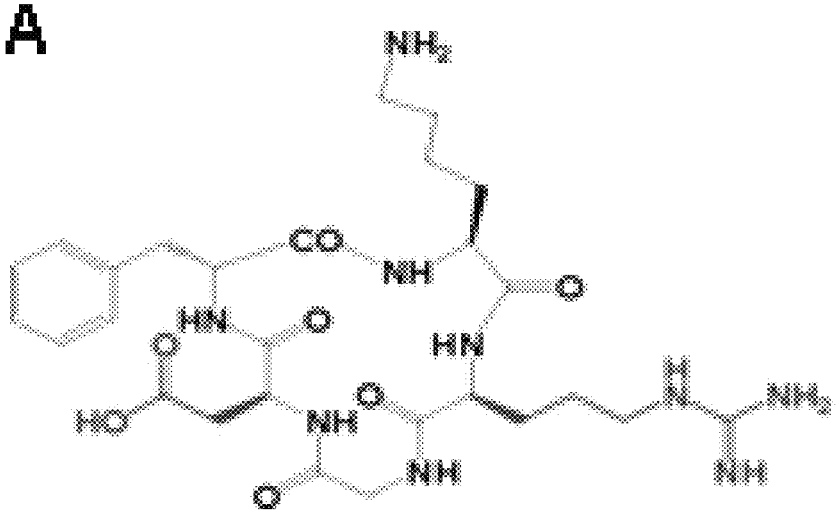
FIG. 17A shows the structure of cRGDfK (an $\alpha_v\beta_3$ ligand).
Figure 17B:
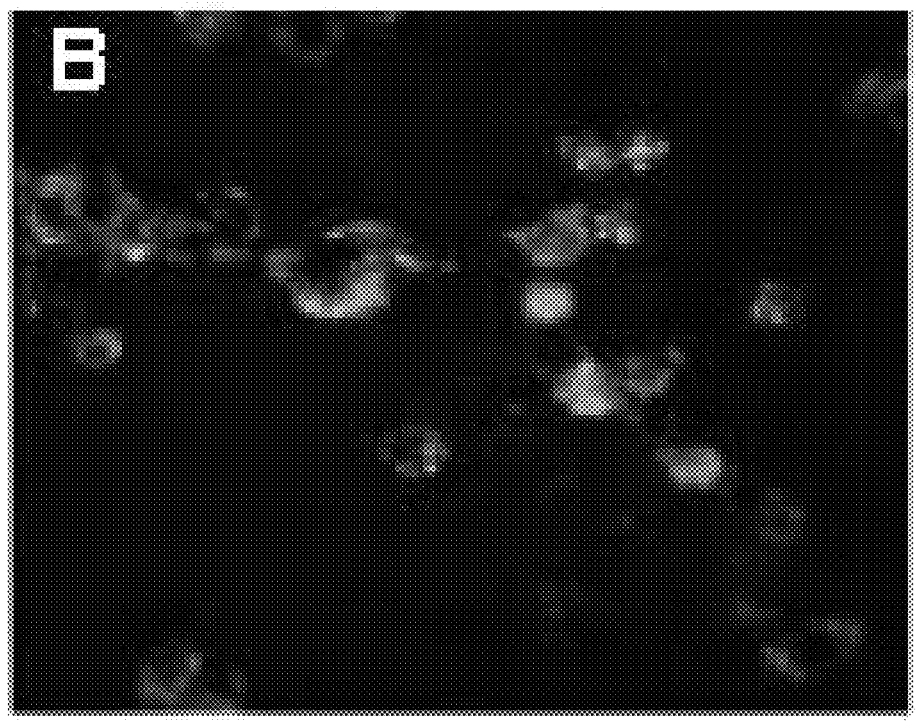
FIG. 17B shows a confocal fluorescence image of MDA-MB-435 cell treated with cRGD-conjugated FITC PAA NP's. The image using the conjugate is excellent.
Figure 17C:
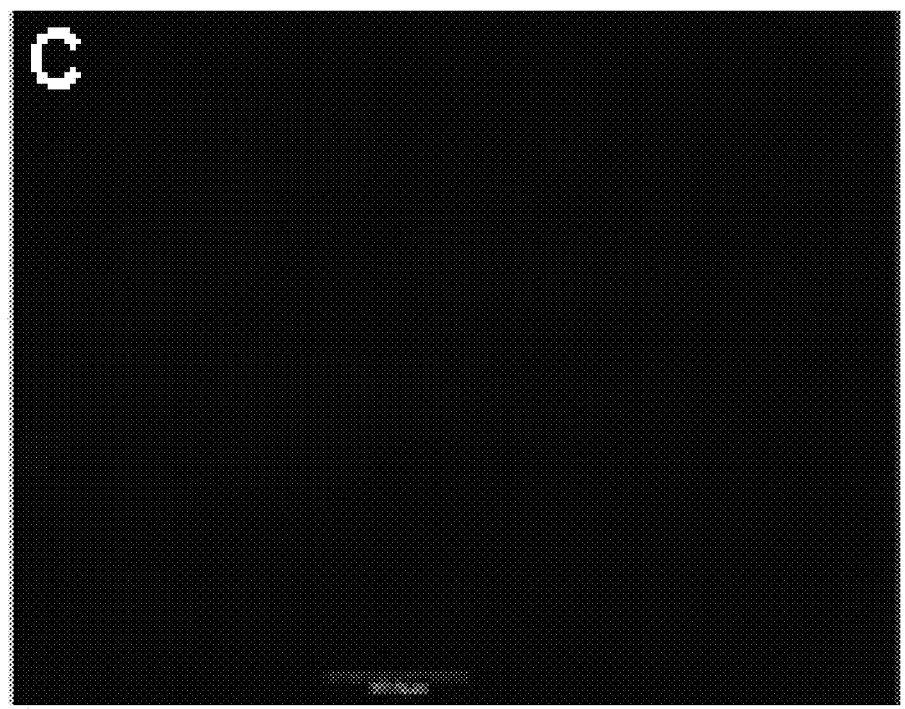
FIG. 17C shows fluorescence image of MDA-MB-435 cells treated with unmodified FITC PAA NP's. The image shows no cell distinction.
Figure 18:
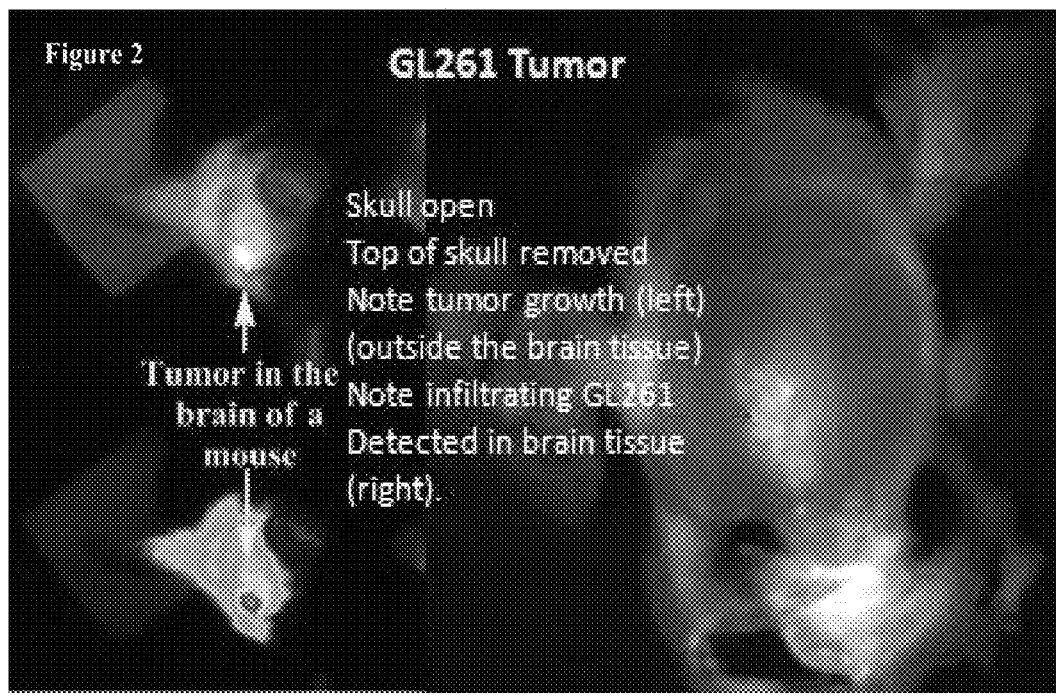
FIG. 18 shows an image of tumor growth in the brain of a mouse using photosensitizer and cyanine dye with PAA nanoparticles.
Figure 21:
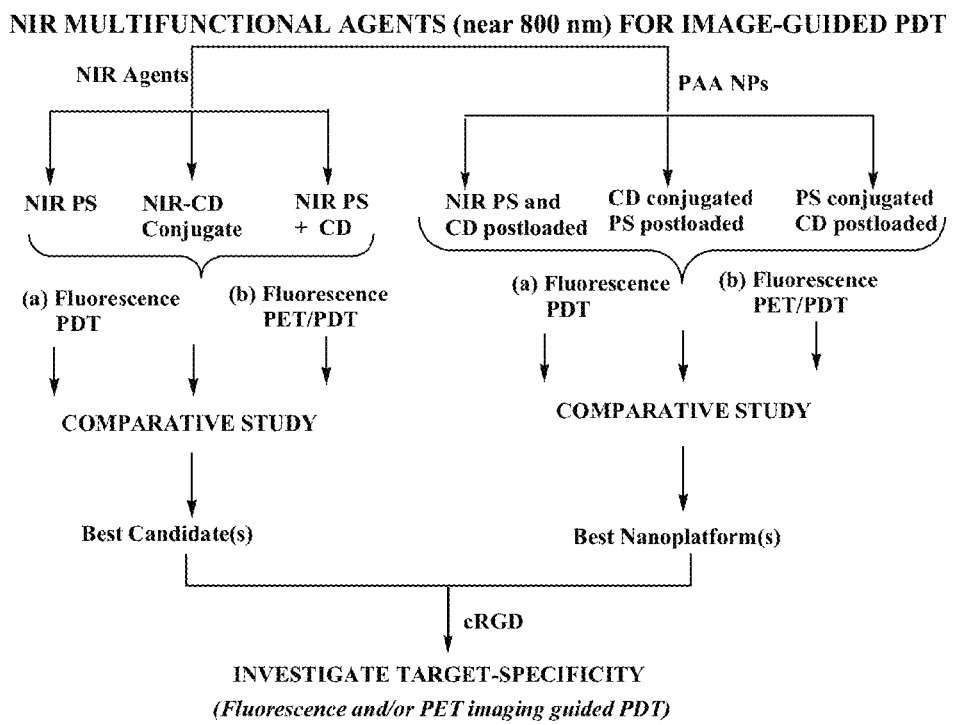
Figure 22:
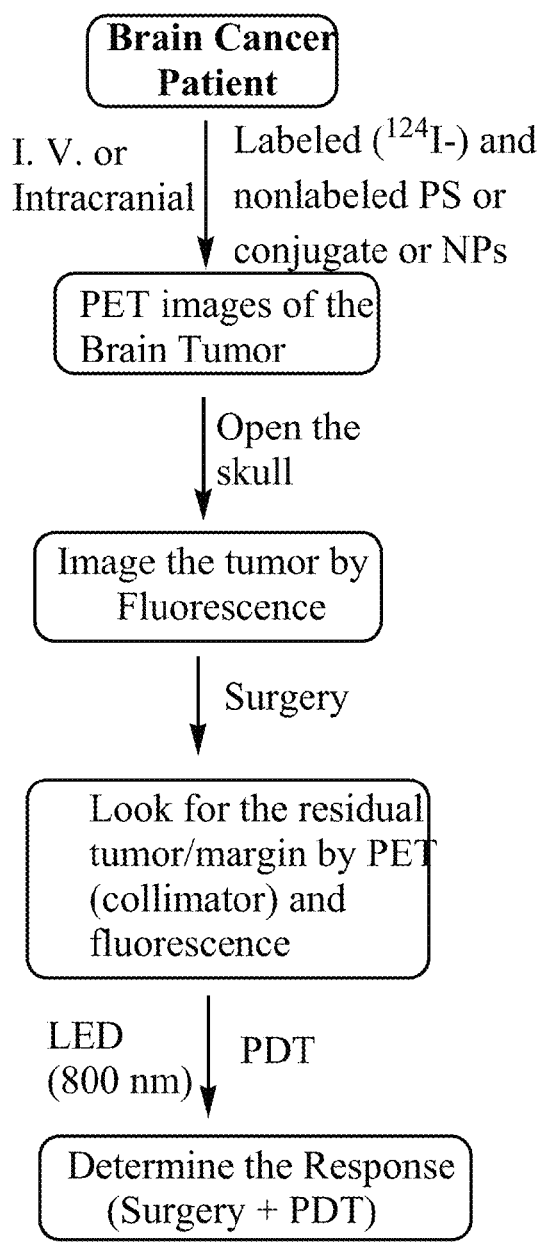

Aim 2: Conjugate cRGD to the best candidate selected from each series (Aims 1 & 2) and compare their target-specificity/pharmacokinetics and PDT efficacy in U87 ($\alpha m\beta_3+$), GL261 (($\alpha_v\beta_3$ low) and A431($\alpha_v\beta_3-$) tumors. Specificity, we prepared FITC conjugated PAA NPs and then attached cRGDfK (an $\alpha_v\beta_3$ ligand), see structure in FIG. 17B, on the surface of the NPs. To test if the surface-modified NPs selectively target tumor tissue, as compared to the unmodified NPs, we treated MDA-435 cells ($\alpha_v\beta_3$ expressing) with both types of NPs (20 min incubation at 0.1 mg/mL). The RGD-conjugated NPs specifically bound to MDA-435 cells but not the unmodified NPs [FIG. 17B and 17C, respectively]. These results indicate that cRGD modified PAA NPs may enable the targeted delivery of incorporated image contrast agents or drugs for imaging and therapy. Specifically, FIG. 17A shows structure of cRGDfK. FIG. 17B shows a confocal fluorescence image of MDA-MB-435 cell treated with cRGD-conjugated FITC PAA NP's and FIG. 17C shows fluorescence image of MDA-MB-435 cells treated with unmodified FITC PAA NP's. Recent results obtained show great potential of combined PS (660 nm) and CD either in a form of conjugates or post-loaded to biocompatible PAA NPs, for tumor-imaging (FIG. 18, $\lambda_{exc}$:783 nm, $\lambda_{em}$ 865 nm) and PDT. This approach can be extended to develop brain cancer target-specific multifunction agents (800 nm agents) for image-guided (PET/fluorescence) PDT. The approach is illustrated in Chart-1 FIG. 21. The best agent(s) selected from this study can be translated in the future to cancer patients by following an approach shown in Chart 2, FIG. 22.

We have developed a novel post-loading approach for constructing a multifunctional biodegradable PAA nanoplatform for tumor-imaging and PDT. This approach provides an opportunity to post-load both imaging and therapeutic agents at desired concentrations. HPPH (a chlorophyll-a derivative, developed in our laboratory and in Phase I/II human clinical trials) was used as a substrate. We have also shown that, compared to free $^{124}$I-PS, the $^{124}$I-PS post-loaded in PAA NPs shows enhanced tumor uptake/tumor imaging and reduced uptake in other organs (especially spleen and liver). We also confirmed the tumor-avidity of PAA NPs by covalently conjugating with a non-tumor avid fluorophore Compound 2, FIG. 19B. Finally, one of the main concerns of using nanoparticles has been their unknown toxicity in vivo. We have evaluated the toxicity of PAA NPs at variable doses and even at a high dose no normal organ toxicity was observed in BALB/c mice. On the basis of our exciting findings we hypothesize that extending these approaches by using near 800 nm PS will produce improved PAA nanoplatforms for imaging brain and other tumors. Various approaches for the preparation of multifunctional NP's are shown in FIGS. 20A-20D.

Figure 19A:
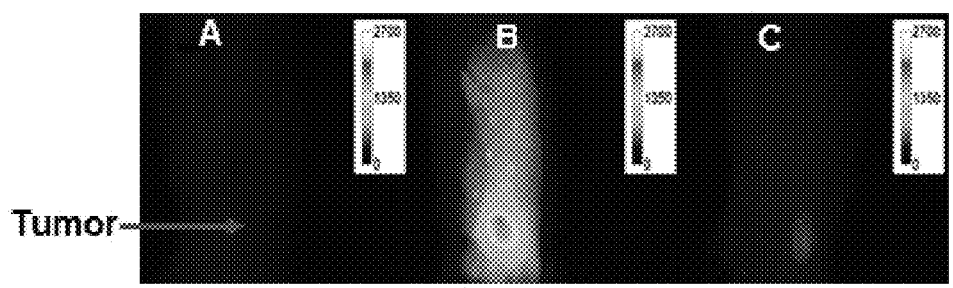
FIG. 19A at A shows a fluorescence image of a control at A with no cyanine dye.
Figure 19B:
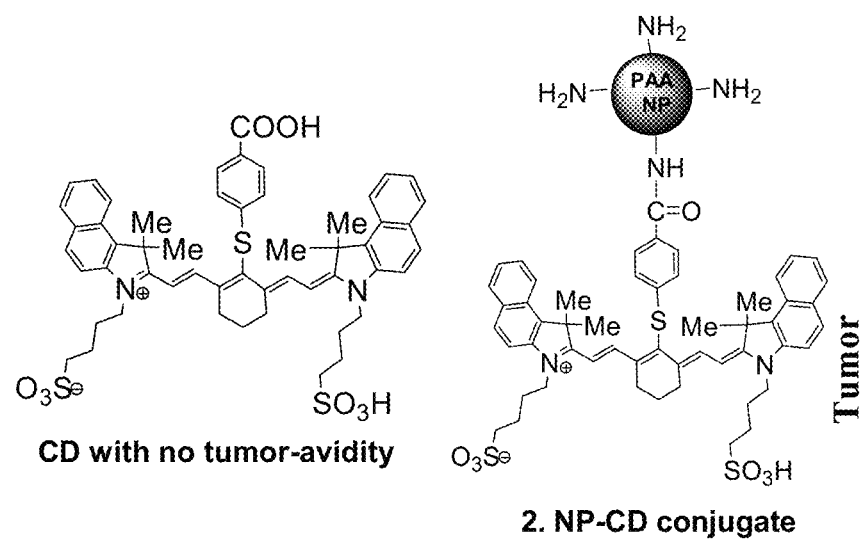
FIG. 19B shows structural formulas for cyanine dye (CD) which showed no tumor avidity and compound 2 conjugate of cyanine dye with an amine containing PAA nanoparticle.
Figure 20A:
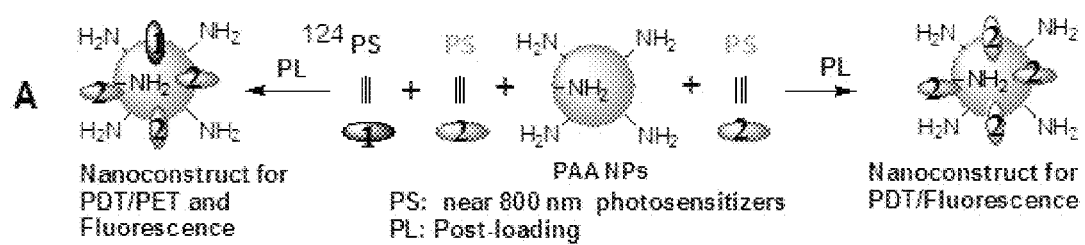
FIGS. 20A through 20B show schemes for various approaches for preparation of multifunctional nanoparticles.
Figure 20B:
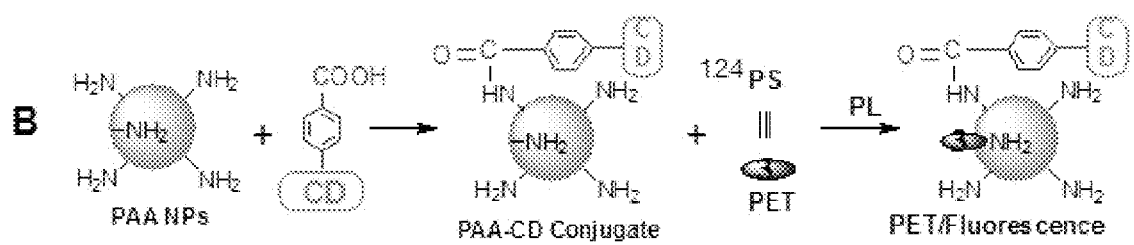
Figure 20C:
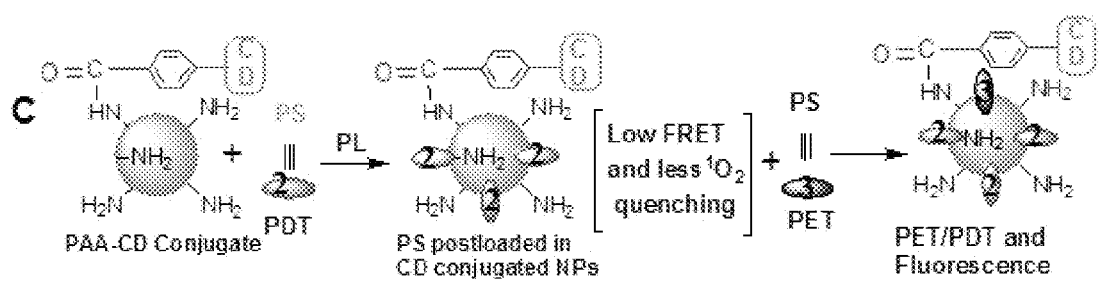
Figure 20D:
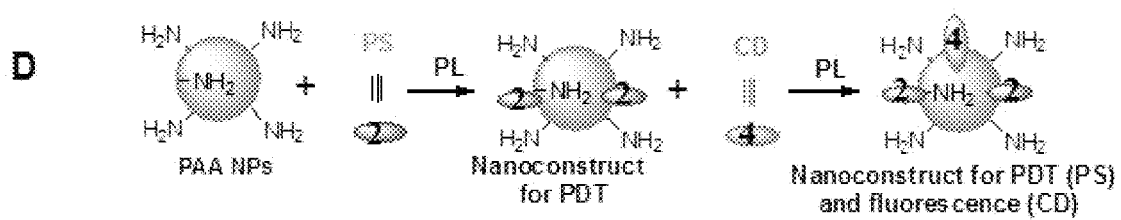

Conjugation of NIR fluorophore at the periphery of PAA NPs drastically enhances its imaging capability: In this approach to investigate the utility of PAA NPs in tumor-specificity, a cyanine dye (CD) containing a carboxylic acid group (FIG. 19B), which did not show any tumor uptake by itself (C in FIG. 19A), was conjugated at the periphery of the PAA NPs (FIG. 19B containing amino functionalities) and the imaging potential of all three preparations was investigated in BALB/c mice bearing Colon26 tumors. The CD-PAA conjugate 2, in FIG. 19A at B, showed the best tumor localization at both 24 and 48 h post injection B in FIG. 19A (only 48 h images are shown). In particular, FIG. 19A shows a control at A, cyanine dye-COOH conjugated to PAA nanoparticles (conjugate 2 48 h post injection) at B and free cyanine dye-COOH (48 h post-injection) at C. Dosages for B and C were 0.3 μmole/kg. FIG. 19B shows structures for cyanine dye and cyanine dye-nanoparticle conjugate.

What is claimed is:

1. A composition comprising: PAA (polyacrylic acid) nanoparticles functionalized with amine groups and containing a tumor targeting tetrapyrrolic photosensitizer postloaded onto the PAA nanoparticles after formation of the nanoparticles and an imaging agent covalently bonded to the PAA nanoparticles and a tumor targeting moiety covalently bonded to the PAA nanoparticles.

2. The composition of claim 1 wherein the tetrapyrrolic photosensitizer has the structural formula:

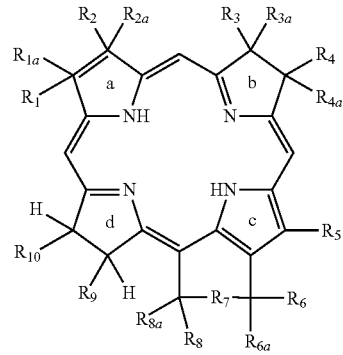

or a pharmaceutically acceptable derivative thereof, wherein:

$R_1$ and $R_2$ are each independently substituted or unsubstituted alkyl, substituted or unsubstituted alkenyl, —C(O) $R_a$ or —COOR$_a$ or —CH(CH$_3$)(OR$_a$) or —CH(CH$_3$)(O (CH$_2$)$_n$XR$_a$) where R$_a$ is hydrogen, substituted or unsubstituted alkyl, substituted or unsubstituted alkenyl, substituted or unsubstituted alkynyl, or substituted or unsubstituted cycloalkyl; where $R_2$ may be —CH=CH$_2$, —CH(OR$_{20}$)CH$_3$, —C(O)Me, —C(=NR$_{21}$)CH$_3$ or —CH(NHR$_{21}$)CH$_3$ where X is an aryl or heteroaryl group;

n is an integer of 0 to 6;

where $R_{20}$ is methyl, butyl, heptyl, docecyl or 3,5-bis(trifluoromethyl)-benzyl; and $R_{21}$ is 3,5,-bis(trifluoromethyl)benzyl;

$R_{1a}$ and $R_{2a}$ are each independently hydrogen or substituted or unsubstituted alkyl, or together form a covalent bond;

$R_3$ and $R_4$ are each independently hydrogen or substituted or unsubstituted alkyl;

$R_{3a}$ and $R_{4a}$ are each independently hydrogen or substituted or unsubstituted alkyl, or together form a covalent bond;

$R_5$ is hydrogen or substituted or unsubstituted alkyl;

$R_6$ and $R_{6a}$ are each independently hydrogen or substituted or unsubstituted alkyl, or together form =O;

$R_7$ is a covalent bond, alkylene, azaalkyl, or azaaraalkyl or =NR$_{20}$ where R$_{20}$ is 3,5-bis(tri-fluoromethyl)benzyl or —CH$_2$X—R$^1$ or —YR$^1$ where Y is an aryl or heteroaryl group;

$R_8$ and $R_{8a}$ are each independently hydrogen or substituted or unsubstituted alkyl or together form =O;

$R_9$ and $R_{10}$ are each independently hydrogen, or substituted or unsubstituted alkyl and $R_9$ may be —$CH_2CH_2COOR^2$ where $R^2$ is an alkyl group that may optionally substituted with one or more fluorine atoms;

each of $R_1$-$R_{10}$, when substituted, is substituted with one or more substituents each independently selected from Q, where Q is alkyl, haloalkyl, halo, photosensitizereudohalo, or —$COOR_b$ where $R_b$ is hydrogen, alkyl, alkenyl, alkynyl, cycloalkyl, aryl, heteroaryl, araalkyl, or $OR_c$ where $R_c$ is hydrogen, alkyl, alkenyl, alkynyl, cycloalkyl, or aryl or $CONR_dR_e$ where $R_d$ and $R_e$ are each independently hydrogen, alkyl, alkenyl, alkynyl, cycloalkyl, or aryl, or $NR_fR_g$ where $R_f$ and $R_g$ are each independently hydrogen, alkyl, alkenyl, alkynyl, cycloalkyl, or aryl, or =$NR_h$ where $R_h$ is hydrogen, alkyl, alkenyl, alkynyl, cycloalkyl, or aryl, or is an amino acid residue;

each Q is independently unsubstituted or is substituted with one or more substituents each independently selected from $Q_1$, where $Q_1$ is alkyl, haloalkyl, halo, photosensitizereudohalo, or —$COOR_b$ where $R_b$ is hydrogen, alkyl, alkenyl, alkynyl, cycloalkyl, aryl, heteroaryl, araalkyl, or $OR_c$ where $R_c$ is hydrogen, alkyl, alkenyl, alkynyl, cycloalkyl, or aryl or $CONR_dR_e$ where $R_d$ and $R_e$ are each independently hydrogen, alkyl, alkenyl, alkynyl, cycloalkyl, or aryl, or $NR_fR_g$ where $R_f$ and $R_g$ are each independently hydrogen, alkyl, alkenyl, alkynyl, cycloalkyl, or aryl, or =$NR_h$ where $R_h$ is hydrogen, alkyl, alkenyl, alkynyl, cycloalkyl, or aryl, or is an amino acid residue wherein the photosensitizer is postloaded onto the nanoparticle after nanoparticle formation.

3. The composition of claim 2 wherein the imaging agent is a cyanine dye.

4. The composition of claim 3 wherein the imaging agent is a $^{124}I$ labeled compound.

5. The composition of claim 3 wherein the imaging agent is a PET, fluorescence or MR imaging agent.

6. The composition of claim 2 wherein the targeting moiety is a peptide, folic acid or a carbohydrate.

7. The composition of claim 1 where the photosensitizer is HPPH.

8. The composition of claim 1 where the numerical ratio of postloaded photosensitizer to imaging agent is from 1 to 1 to 10 to 1.

9. The composition of claim 8 where the numerical ratio of postloaded photosensitizer moieties to imaging agent is from 2 to 1 to 4 to 1.

10. The composition of claim 1 where the photosensitizer is a HPPH, purpurinimide having an absorbance between 680 and 720 nm, bacteriopurpurinimide having an absorbance between 780 and 800 nm or mixtures thereof.

11. The nanoparticle of claim 1 where the tetrapyrrolic photosensitizer has an emission between 700 and 800 nm.

12. The nanoparticle of claim 1 where the tumor targeting agent is an RGD peptide.

13. The composition of claim 1 wherein the targeted moiety is cRGD or F3 or F3-targeted (A series), F3-Cys targeted (B series), peptide, folic acid or a carbohydrate.

14. A method for making PAA (polyacrylic acid) nanoparticles functionalized with amine groups according to claim 1 by covalently bonding a fluorophore imaging agent and a tumor targeting moiety onto pre-prepared PAA nanoparticles functionalized with amine groups and then post loading a tetrapyrrolic photosensitizer onto the pre-prepared PAA nanoparticles.

15. The method of claim 14 where the photosensitizer is HPPH.

16. A method for imaging and treatment of hyperproliferative tissue in an animal comprising: a) injecting PAA (polyacrylic acid) nanoparticles functionalized with amine groups and containing a tumor targeting tetrapyrrolic photosensitizer postloaded onto the PAA nanoparticles after formation of the nanoparticles and an imaging agent covalently bonded to the PAA nanoparticles and a tumor targeting moiety covalently bonded to the PAA nanoparticles composition according to claim 1 in an amount of 0.05 to 1.0 μmoles/kg, b) imaging the animal utilizing the covalently bonded imaging agent to define and locate the hyperproliferative tissue, and c) treating the defined and located hyperproliferative tissue with photodynamic therapy.

17. A method for imaging and treatment of hyperproliferative tissue in an animal comprising: a) injecting a composition according to claim 5 in an amount of 0.05 to 1.0 μmoles/kg, b) imaging the animal utilizing the covalently bonded imaging agent to define and locate the hyperproliferative tissue, and c) treating the defined and located hyperproliferative tissue with photodynamic therapy.

18. A method for imaging and treatment of hyperproliferative tissue in an animal comprising: a) injecting a composition according to claim 1 in an amount of 0.05 to 1.0 μmoles/kg b) imaging the animal utilizing the covalently bonded imaging agent to define and locate the hyperproliferative tissue, and c) treating the defined and located hyperproliferative tissue with photodynamic therapy.

* * * * *